United States Patent [19]

Peglion et al.

[11] Patent Number: 4,885,373
[45] Date of Patent: Dec. 5, 1989

[54] 2,4,5,6,7,8-HEXAHYDRONAPHTHO[2,3-B]FURAN USEFUL AS AN INTERMEDIATE

[75] Inventors: Jean L. Peglion, Le Vesinet; Jean C. Poignant, Bures sur Yvette; Joel Vian, Chaville, all of France

[73] Assignee: ADIR Et Cie, Neuilly-sur-Seine, France

[21] Appl. No.: 303,545

[22] Filed: Jan. 27, 1989

Related U.S. Application Data

[62] Division of Ser. No. 173,285, Mar. 25, 1988, Pat. No. 4,863,951.

[30] Foreign Application Priority Data

Apr. 1, 1987 [FR] France ................... 87 04551

[51] Int. Cl.[4] ........................................... C07D 307/92
[52] U.S. Cl. .................................................. 549/458
[58] Field of Search ........................................ 549/458

[56] References Cited

PUBLICATIONS

Chem. Abstracts 7097i, vol. 50, (1956).

Primary Examiner—Mary C. Lee
Assistant Examiner—Bernard I. Dentz
Attorney, Agent, or Firm—Gordon W. Hueschen

[57] ABSTRACT

Compounds of general formula I,

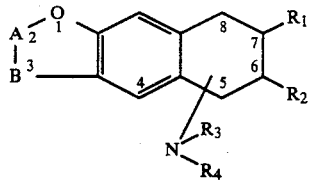

in which:

$R_1$ denotes a hydrogen atom or, with the proviso, however, that the amino radical is at the 7-position, a linear or branched alkyl radical containing 1 to 4 carbon atoms, $R_2$ denotes a hydrogen atom or, with the proviso, however, that the amino radical is at the 6-position, a linear or branched alkyl radical containing 1 to 4 carbon atoms, $R_3$ and $R_4$, which may be identical or different, each denote a hydrogen atom, a benzyl radical, a cyclohexylmethyl radical, a linear or branched alkylene radical containing from 1 to 5 carbon atoms, a linear or branched alkyl radical containing from 1 to 10 carbon atoms (optionally substituted with a hydroxy radical, with a carboxy radical or with an alkoxy radical having 1 to 5 carbon atoms, with an alkoxycarbonyl radical having 2 to 6 carbon atoms, with an alkylphenyl radical or with an alkyl-2-thienyl radical), a halogenated alkyl radical containing from 1 to 5 carbon atoms, or form, together with the nitrogen to which they are attached, a 2-oxo-1-pyrrolidinyl radical, A-B denotes, with the oxygen to which it is attached, an ethyleneoxy radical, an ethynyleneoxy, a 2-oxo-1-oxyethylene radical or a 2-hydroxy-1-oxyethylene radical.

The compounds of Formula I possess antidepressant, antiaggressive, and dopaminergic properties.

1 Claim, No Drawings

2,4,5,6,7,8-HEXAHYDRONAPHTHO[2,3-B]FURAN USEFUL AS AN INTERMEDIATE

This is a divisional of application Ser. No. 173,285, filed Mar. 25, 1988, now U.S. Pat. No. 4,863,951, issued Sept. 5, 1989.

The present invention relates to new amino-5,6,-7,8-tetrahydronaphtho[2,3-b]furan compounds, the processes for preparing them and the pharmaceutical compositions which contain them.

Some pharmacologically active tricyclic compounds derived from aminotetrahydronaphthalene are known. In effect, a few compounds of 7,8,9,10-tetrahydrobenzo[h]quinol-9-ylamine, whose antidepressant activity has been assessed only by in vitro tests, are mentioned in the literature (U.S. Pat. No. 4,521,423). 6,7,8,9-Tetrahydrobenzo[g]indol-8-ylamines and 6,7,8,9-tetrahydronaphtho-[1,2-b]furan-8-ylamines endowed with dopaminergic stimulatory activity are described in U.S. Pat. Nos. 4,510,157 and 4,470,990.

The Applicant has now discovered that some compounds of amino-5,6,7,8-tetrahydronaphtho[2,3-b]furan, of novel structure, are endowed with very advantageous pharmacological properties. In effect, the compounds of the present invention possess considerably antidepressant and psychostimulatory activity, demonstrated by in vivo trials, and dopaminergic properties.

The subject of the present invention is, more especially, the compounds of general formula I,

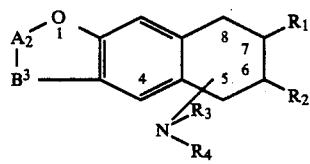
(I)

in which:

$R_1$ denotes a hydrogen atom or, with the proviso, however, that the amino radical is at the 7-position, a linear or branched alkyl radical containing 1 to 4 carbon atoms, $R_2$ denotes a hydrogen atom or, with the proviso, however, that the amino radical is at the 6-position, a linear or branched alkyl radical containing 1 to 4 carbon atoms, $R_3$ and $R_4$, which may be identical or different, each denote a hydrogen atom, a benzyl radical, a cyclohexylmethyl radical, a linear or branched alkylene radical containing from 1 to 5 carbon atoms, a linear or branched alkyl radical containing from 1 to 10 carbon atoms (optionally substituted with a hydroxy radical, with a carboxy radical or with an alkoxy radical having 1 to 5 carbon atoms, with an alkoxycarbonyl radical having 2 to 6 carbon atoms, with an alkylphenyl radical having 7 to 16 carbon atoms or with an alkyl-2-thienyl radical having 5 to 14 carbon atoms) or a halogenated alkyl radical containing from 1 to 5 carbon atoms, or form, together with the nitrogen to which they are attached, a 2-oxo-1-pyrrolidinyl radical, A-B denotes, with the oxygen to which it is attached, a radical

—CH$_2$—CH$_2$—O—, or, with the proviso, however, that the amino radical is at the 7-position and $R_1$ denotes a hydrogen atom, a radical

—CH=CH—O—, a radical

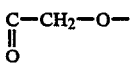

or a radical

—CH—CH$_2$—O—,
  |
  OH in racemic form or in the form of optical isomers, and their addition salts with a pharmaceutically acceptable inorganic or organic acid.

The subject of the present invention is also the process for preparing with the compounds of general formula I, wherein:
either
2,3-dihydrobenzofuran of formula II,

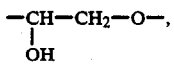
(II)

is condensed with succinic anhydride in the presence of aluminum chloride in a chlorinated organic solvent and at a temperature below 5° C., to form 4-(2,3-dihydro-5-benzofuranyl)-4-oxobutanoic acid of formula III,

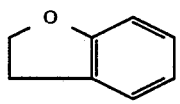
(III)

which is reduced in acid medium in the heated state and in the presence of zinc and mercuric chloride to form 4-(2,3-dihydro-5-benzofuranyl)butanoic acid of formula IV,

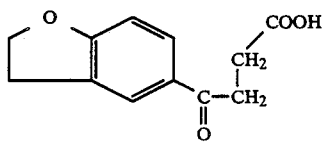
(IV)

which is then subjected to the action of polyphosphoric acid in an apolar organic solvent and at a temperature of between 80° C. and 100° C. to form 2,3,5,6,7,8-hexahydronaphtho[2,3-b]furan-8-one of formula V,

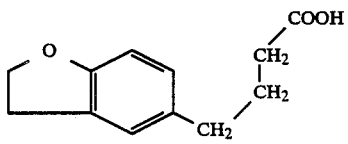
(V)

which is then:

either
subjected to the action of a hydroxylamine salt, in the heated state, in a low molecular weight alcohol, to form 2,3,5,6,7,8-hexahydronaphtho[2,3,-b]furan-8-one oxime of formula VI,

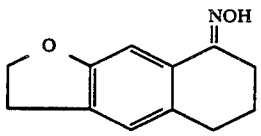

which is then:
either
condensed with para-toluenesulfonyl chloride in a basic organic medium and at a temperature below 5° C. to form 2,3,5,6,7,8-hexahydronaphtho[2,3-b]furan-8-one oxime para-toluenesulfonate of formula VII,

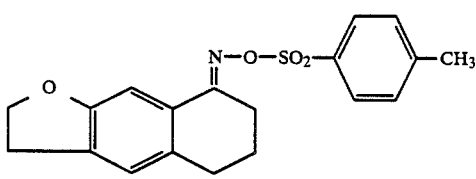

which is reacted with sodium ethanolate in an anhydrous apolar organic solvent at a temperature of approximately 0° C. to form 7-acetylamino-2,3,5,6,7,8-hexahydronaphtho-[2,3-b]furan-8-one of formula VIII,

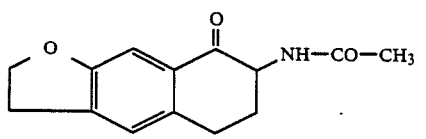

which is subjected to a hydrogenation at room temperature in the presence of an acid and palladium on charcoal (5% palladium) to form 7-acetylamino-2,3,5,6,7,8-hexahydronaphtho[2,3-b]furan of formula IX,

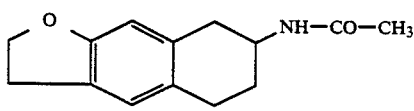

which is then converted by acid hydrolysis in the heated state to 7-amino-2,3,5,6,7,8-hexahydronaphtho[2,3-b]furan of formula Ia,

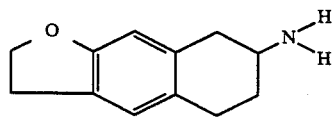

which can then be alkylated to form the corresponding secondary or tertiary amines,
either by condensing it with a compound of general formula X,

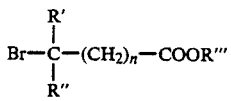

in which
R' and R'', which may be identical or different, each denote a hydrogen atom or a lower alkyl radical having 1 to 4 carbon atoms,
R''' denotes a lower alkyl radical having 1 to 5 carbon atoms, and
n is an integer from 0 to 9, to form a compound of general formula Ia₁,

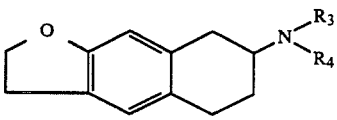

in which
R₄ denotes a hydrogen and
R₃ denotes a linear or branched alkyl radical having 1 to 10 carbon atoms and substituted with an alkoxycarbonyl radical having 2 to 6 carbon atoms, which can then be subjected to the action of a strong inorganic base to form a compound of general formula Ia₁,
in which
R₄ denotes a hydrogen and
R₃ denotes a linear or branched alkyl radical having 1 to 10 carbon atoms and substituted with a carboxy radical, which can then be subjected to the action of a double metal hydride to form a compound of general formula Ia₁
in which
R₄ denotes a hydrogen and
R₃ denotes a linear or branched alkyl radical having 1 to 10 carbon atoms and substituted with a hydroxy radical,
or by reacting it with an acid chloride of general formula Xi, $$W(CH_2)_nCOCl \qquad (XI)$$

in which
n is an integer from 0 to 9 and
W denotes a phenyl radical or a 2-thienyl radical, or W(CH₂)ₙ denotes a halogenated alkyl radical containing from 1 to 5 carbon atoms, and then reducing the compound resulting from this reaction with a double metal hydride to form a compound of general formula Ia₁
in which
R₃ denotes an alkyl radical having 1 to 10 carbon atoms and substituted with a phenyl radical or a 2-thienyl radical, or a halogenated alkyl radical containing from 1 to 5 carbon atoms, and
R₄ denotes a hydrogen atom,
or by reacting it with a sufficient quantity of formaldehyde and formic acid to obtain the compounds of the general formula Ia₁ in which R₃ and R₄ are identical and each denote a methyl radical,
or by reacting it with 4-chlorobutyryl chloride to form, after a condensation by means of a metal hydride, a compound of general formula Ia₁ in which R₃ and R₄ form, together with the nitrogen to which they are attached, a 2-oxo-1-pyrrolidinyl radical, or by reacting it with an alkyl iodide or chloride of general formula XII$_a$ and XII$_b$, IR                            (XIIa)

ClR                        (XIIb)

in which R denotes a linear or branched alkyl radical containing from 1 to 10 carbon atoms (optionally substituted with a hydroxy radical or with an alkoxy radical having 1 to 5 carbon atoms) or a cyclohexylmethyl radical, in the heated state in an organic solvent and in the presence of an inorganic base, to form the compounds of general formula Ia$_1$ in which R$_3$ and R$_4$ are identical and have the same meaning as R, or by subjecting it to the action of benzaldehyde in the heated state and in the presence of a low molecular weight alcohol to form the corresponding benzylimine, and then to a catalytic hydrogenation and thereafter to the action of formic acid and formaldehyde to form the compounds of general formula Ia$_1$ in which R$_3$ denotes a methyl radical and R$_4$ a cyclohexylmethyl radical, or by subjecting it first to the action of benzaldehyde in the presence of an inert and apolar aromatic solvent and then, after removal of the solvent used, to the action of sodium borohydride in the presence of a low molecular weight polar aliphatic alcohol, to obtain a compound of general formula Ia$_1$ in which R$_3$ denotes a hydrogen and R$_4$ a benzyl radical, which can then be subjected: either to the action of formaldehyde and formic acid to form the compounds of general formula Ia in which R$_3$ denotes a methyl radical and R$_4$ a benzyl radical, or to the action of an alkyl iodide of general formula XIIa$_1$ to form the compounds of general formula Ia$_1$ in which R$_3$ has the same meaning as R and R$_4$ denotes a benzyl radical, which can then be subjected to a catalytic hydrogenation to form the compounds of general formula Ia$_1$ in which R$_3$ has the meaning given above and R$_4$ denotes a hydrogen atom, which can then be subjected to the action of an alkyl iodide of general formula XIIa to form the compounds of general formula Ia$_1$ in which R$_3$ and R$_4$, which may be identical or different, each denote an alkyl radical containing from 1 to 10 carbon atoms (optionally substituted with a hydroxy radical or an alkoxy radical having 1 to 5 carbon atoms) or a cyclohexylmethyl radical, or subjected to a catalytic hydrogenation in the presence of palladium on charcoal (5% palladium) at room temperature, to obtain 8-amino-2,3,5,6,7,8-hexahydronaphtho-[2,3-b]furan of formula Ib,

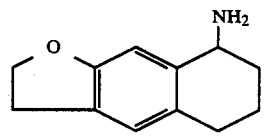

which can then be alkylated according to the methods described above for the compounds of general formula Ia to form the corresponding secondary or tertiary amines of general formula Ib$_1$,

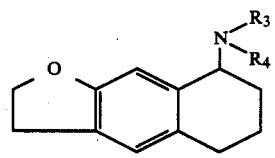

in which R$_3$ and R$_4$ have the meaning given above for the general formula I, except that they never simultaneously denote a hydrogen atom, or subjected to the action of an excess of pyridinium bromide perbromide in a chlorinated polar organic solvent and at a temperature close to 0° C. to form 7,7-dibromo-2,3,5,6,7,8-hexahydronaphtho[2,3-b]furan-8-one of formula XIII

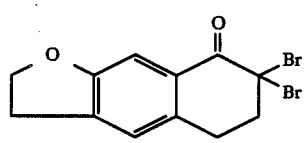

which is then condensed with a linear or branched alkylmagnesium iodide containing 1 to 4 carbon atoms, in the presence of copper bromide, in an anhydrous organic solvent and at a temperature of between −20° C. and −40° C., to form the compounds of general formula XIV,

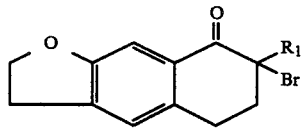

in which the meaning R$_1$ is that given for the general formula I, which is reacted with sodium azide in an acid organic medium and at a temperature of approximately 0° C. to form a 7-azido-7-alkyl-2,3,5,6,7,8-hexahydronaphtho[2,3-b]furan-8-one compound of general formula XV,

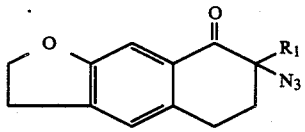

in which R$_1$ has the same meaning as above, which is then reduced by means of sodium borohydride in an anhydrous alcoholic solvent to form a 7-azido-7-alkyl-8-hydroxy-2,3,5,6,7,8-hexahydronaphtho[2,3-b]furan compound of general formula XVI

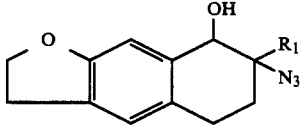

in which the meaning of R$_1$ is identical to that given above, which is then subjected to the action of triethylsilane in the presence of trifluoroacetic acid under an inert atmosphere to form a 7-azido-7-alkyl-2,3,5,6,7,8- hexahydronaphtho[2,3-b]furan compound of general formula XVII

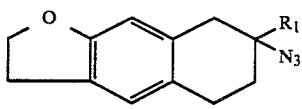

(XVII)

in which $R_1$ has the same meaning as above, and which is reacted with hydrazine in the presence of Raney nickel in anhydrous medium to form the compounds of general formula Ic,

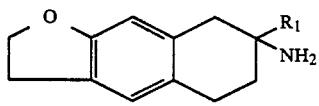

(Ic)

in which the meaning of $R_1$ remains identical to that stated above, which compounds can then be alkylated according to the methods described for the alkylation of the compound Ia, to form the corresponding secondary or tertiary amines of general formula $Ic_1$,

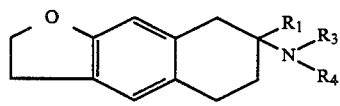

($Ic_1$)

in which
$R_1$ has the meaning stated above, and
$R_3$ and $R_4$ have the meaning given for the general formula I, except that they never simultaneously denote a hydrogen atom,
or
reduced by means of an amalgam of metallic zinc and mercuric chloride in acid medium and in the heated state to form 2,3,5,6,7,8-hexahydronaphtho[2,3-]furan of formula XVIII,

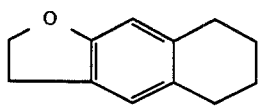

(XVIII)

which is oxidized by means of chromic anhydride in an organic acid medium and at a temperature below 5° C. to form 2,3,5,6,7,8-hexahydronaphtho[2,3-b]furan-5-one of formula XIX,

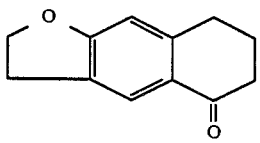

(XIX)

which is then,
either
condensed with a hydroxylamine salt at a temperature of approximately 100° C., in a low molecular weight alcohol, to form 2,3,5,6,7,8-hexahydronaphtho[2,3-b]furan-5-one oxime of formula XX,

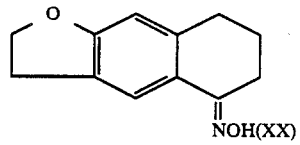

NOH(XX)

which is then subjected to a catalytic hydrogenation at room temperature in the presence of palladium on charcoal (5% palladium) to form 5-amino-2,3,5,6,7,8-hexahydronaphtho[2,3-b]furan of formula Id,

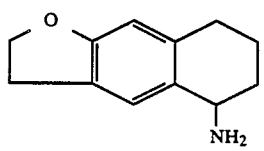

(Id)

which can then be alkylated according to the methods described for the alkylation of the compound Ia, to form the corresponding secondary or tertiary amines of general formula $Id_1$,

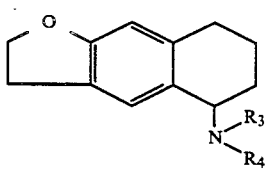

($Id_1$)

in which $R_3$ and $R_4$ have the same meaning as in the general formula I, except that they never simultaneously denote a hydrogen atom,
either
subjected to the action of a sufficient quantity of pyridinium bromide perbromide in a polar organic solvent to form a compound of general formula XXI,

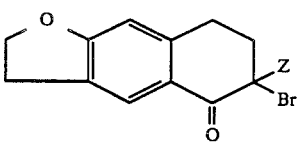

(XXI)

in which Z denotes a hydrogen atom when the quantity of pyridinium bromide perbromide used is approximately equimolar, or a bromine atom when the bromination reaction has been performed with at least double the quantity of brominating reagent, which is then condensed, when it contains two bromine atoms at the 6-position, first with a linear or branched alkylmagnesium iodide containing from 1 to 4 carbon atoms, in the presence of copper bromide, and then reacted with sodium azide, or
reacted directly with sodium azide when Z denotes a hydrogen atom, to form a 6-azido-2,3,5,6,7,8-hexahydronaphtho[2,3-b]furan-5-one compound of general formula XXII,

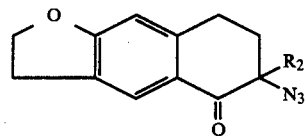
(XXII)

in which R$_2$ denotes a hydrogen atom, which is then reduced by means of sodium borohydride in the presence of an anhydrous alcoholic solvent to form a 6-azido-5-hydroxy-2,3,5,6,7,8-hexahydronaphtho[2,3-b]furan compound of general formula XXIII,

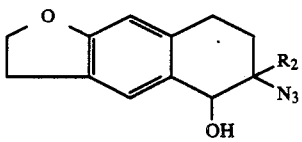
(XXIII)

in which R$_2$ has the meaning stated above, which is then subjected to the action of triethylsilane in the presence of trifluoroacetic acid under an inert atmosphere to form a 6-azido-2,3,5,6,7,8-hexahydronaphtho-[2,3-b]furan compound of general formula XXIV,

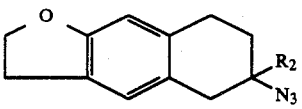
(XXIV)

in which the meaning of R$_2$ remains identical to that given above, which is then reacted with hydrazine in the presence of Raney nickel in anhydrous medium to form a 6-amino-2,3,5,6,7,8-hexahydronaphtho[2,3-b]furan compound of general formula Ie,

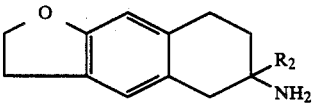
(Ie)

in which R$_2$ has the meaning stated above, which can then be alkylated according to the methods described above for the alkylation of the compound Ia, to form the corresponding secondary or tertiary amines of general formula Ie$_1$,

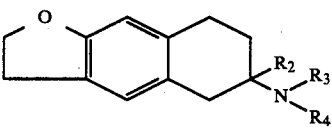
(Ie$_1$)

in which R$_2$, R$_3$ and R$_4$ have the same meaning as in the general formula I except that R$_3$ R$_4$ never simultaneously denote a hydrogen atom,
or
2,7-dimethoxynaphthalene of formula XXV,

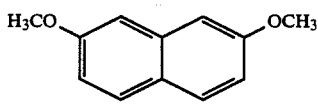
(XXV)

is subjected to the action of sodium metal, in the heated state and in the presence of an anhydrous alcohol, to form 7-methoxy-1,2,3,4-tetrahydro-2-naphthalenone of formula XXVI,

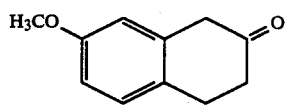
(XXVI)

which is then reacted in the heated state in an alcoholic solvent with a hydroxylamine salt to form 7-methoxy-1,2,-3,4-tetrahydro-2-naphthalenone oxime of formula XXVII,

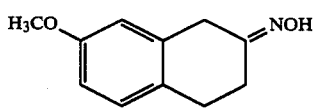
(XXVII)

which is then subjected to a catalytic hydrogenation, in solution in an alcohol, in the presence of Raney nickel and ammonia, to form 2-amino-7-methoxy-1,2,3,4-tetrahydronaphthalene of formula XXVIII,

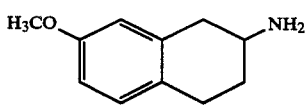
(XXVIII)

which is condensed with acetic anhydride in acetic acid medium to form 2-acetamido-7-methoxy-1,2,3,4-tetrahydronaphthalene of formula XXIX,

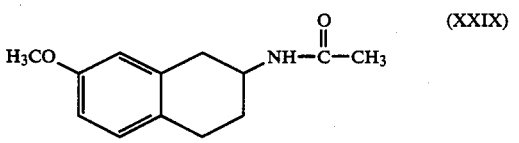
(XXIX)

which is subjected to the action of boron tribromide, at room temperature in a halogenated organic solvent, to form 2-acetamido-7-hydroxy-1,2,3,4-tetrahydronaphthalene of formula XXX,

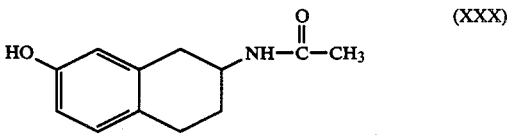
(XXX)

which is then reacted with chloroacetonitrile, in the presence of boron trichloride and aluminum chloride, to form 2-acetamido-6-(2-chloro-1-oxoethyl)-7-hydroxy-1,2,3,4-tetrahydronaphthalene of formula XXXI,

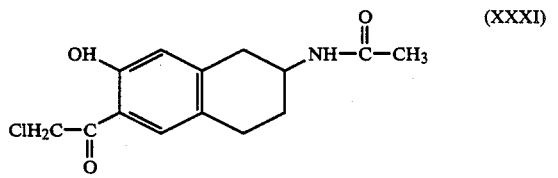
(XXXI)

which is subjected to the action of triethylamine, in the heated state in a halogenated organic solvent, to form 7-acetamido-2,3,5,6,7,8-hexahydronaphtho[2,3-b]furan-3-one of formula XXXII,

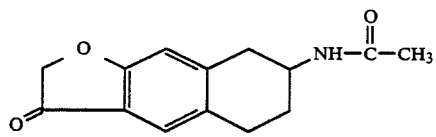
(XXXII)

which is then
either
subjected to the action of a strong inorganic base to form the compound of formula If,

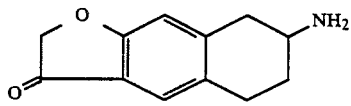
(If)

which can then be alkylated according to the methods described above for the alkylation of the compound Ia to form the compounds of general formula $If_1$,

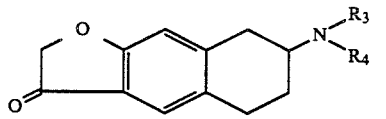
($If_1$)

in which the definition of $R_3$ and $R_4$ is identical to that given for the general formula I, except that $R_3$ and $R_4$ never simultaneously denote a hydrogen atom,
or
reduced in an ethanolic solvent at room temperature with sodium borohydride to form 7-acetamido-3-hydroxy-2,3,5,-6,7,8-hexahydronaphtho[2,3-b]furan of formula XXXIII,

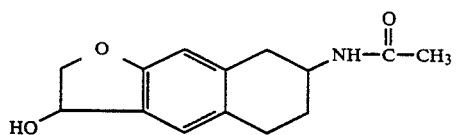
(XXXIII)

which is then subjected,
either
to the action of a strong base to form the compound of formula Ig,

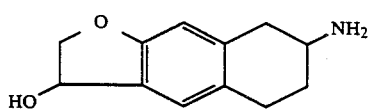
(Ig)

which can then be alkylated according to the processes described above for the compound Ia, to form the compounds of general formula $Ig_1$,

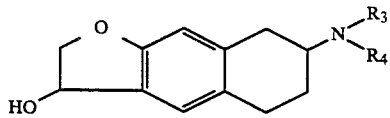
($Ig_1$)

in which $R_3$ and $R_4$ have the same meaning as in the general formula I, except that $R_3$ and $R_4$ never simultaneously denote a hydrogen atom,
or
to the action of a strong inorganic acid at room temperature, to form 7-acetamido-5,6,7,8-tetrahydronaphtho[2,3-b]furan of formula XXXIV,

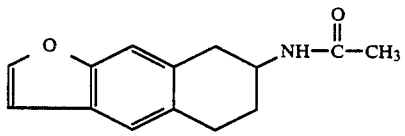
(XXXIV)

which is then subjected to the action of a strong inorganic base in alcoholic medium to form the compound of formula Ih,

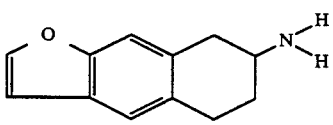
(Ih)

which can then be subjected to an alkylation according to the methods described above for primary amines, to form the compounds of formula $Ih_1$,

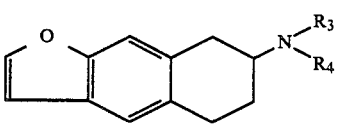
($Ih_1$)

in which the meaning of $R_3$ and $R_4$ is identical to that in the general formula I, except that they never simultaneously denote a hydrogen atom.

The set of compounds of formulae Ia to Ih and $Ia_1$ to $Ih_1$ forms the set of compounds of general formula I, which can be salified with a pharmaceutically acceptable inorganic or organic acid, or first separated into their optical isomers and then optionally salified.

Among pharmaceutically acceptable acids for preparing the addition salts with the compounds of general formula I, hydrochloric, phosphoric, fumaric, citric, oxalic, sulfuric, tartaric, maleic, mandelic and methanesulfonic acids, and the like, may be mentioned.

The compounds of general formula I can be separated into their optical isomers after forming the salts with d- and l-camphorsulfonic, dibenzoyltartaric or tartaric acids. The process for preparing the compounds Ia, Ib and Ic is illustrated in formula sheet No. 1. The process for preparing the compounds Id and Ie is illustrated in formula sheet No. 2 and the process for preparing the compounds If, Ig and Ih is illustrated in formula sheet No. 3.

The formula charts for the process of the invention are found at the end of this specification. The synthesis intermediate 2,3,5,6,7,8-tetrahydronaphtho[2,3-b]furan-5-one (compound of formula XIX) is a new product and accordingly forms part of the present invention.

The compounds according to the invention, as well as their salts and their optical isomers, are endowed with highly advantageous pharmacological properties. In effect, in vivo pharmacological trials have shown that the compounds possess potent antidepressant, antiaggressive and psychostimulatory properties. These properties have been demonstrated by means of tests classically used in animals, enabling the activity in man to be predicted with very great accuracy ("Antidepressants: Neurochemical Behavioral and Clinical Perspectives" Enna S. J., Mallick J., Richelson E., Raven Press Ed., 1981, N.Y. and "Industrial Pharmacology Antidepressants (II" Fielding Stuart, Harbans Lal, Futura Publ. Comp. Ed., 1975 N.Y.).

The results of the pharmacological studies have also demonstrated that the compounds of the invention have a dopaminergic action, the isomers having a more or less intense agonist activity. Recently, it has been found that, in Parkinson's disease, there is a dopamine depletion of the central gray nuclei of the extrapyramidal system. Thus, dopaminergic agonists like the compounds of the present invention can have very advantageous therapeutic effects for the symptomatic treatment of this disease (Burgers Medicinal Chemistry 4th Ed., Part III, p. 413–430, (1981), J. Wiley and Sons Ed.).

Dopamine also exerts a potent restraining effect on the secretion of prolactin, a hormone whose principal action is the development and maintenance of lactogenesis. The compounds of the present invention can hence be used for treating neuroendocrine disorders due to a dopaminergic deficiency, such as hyperprolactinemia and galactorrhea (The Pharmacological basis of Therapeutics, 7th Ed., 1374–1385, Goodman Gilman A. Ed., Macmillan Publish Comp. N.Y.).

The invention also encompasses the pharmaceutical compositions containing, as active principle, at least one compound of general formula I, one of its isomers or one of its salts with a pharmaceutically compatible inorganic or organic acid, in combination with one or more inert and suitable excipients.

The pharmaceutical compositions thereby obtained are advantageously presented in various forms such as, for example, tablets, dragees, gelatin capsules, sublinqual tablets or other galenical preparations suitable for sublingual administration, suppositories, injectable solutions or solutions to be taken by mouth.

The dosage can vary widely according to the patient's age and weight, the nature and severity of the condition and also the administration route.

The preferred administration route is the oral or parenteral route. Generally speaking, the unit dosage will range between 0.5 and 100 mg, and the daily dosage, usable in human therapy, between 10 and 100 mg.

The examples which follow, given without implied limitation, illustrate the invention.

The melting points are measured according to the micro-Kofler technique. The proton nuclear magnetic resonance (NMR) spectra were recorded at 60 MHz.

EXAMPLE 1

2,3,5,6,7,8-Hexahydronaphtho[2,3-]furan-8-one

STAGE A 4-(2,3-Dihydro-5-benzofuranyl)-4-oxobutanoic acid

A susension, cooled to 0° C., of 120 g of 2,3-dihydrobenzofuran and 128 g of aluminum chloride in 260 ml of dichloroethane is added to a mixture of 96 g of succinic anhydride and 260 g of aluminum chloride in 512 ml of dichloroethane. The temperature is maintained at approximately 5° C. The reaction medium, maintained for 2 hours at this temperature, is then poured into a solution of 3 liters of water containing 400 ml of concentrated hydrochloric acid. After separation following settling, and extraction with methylene chloride, the organic phase is exhaustively extracted with 1N sodium hydroxide. The combined basic phases are acidified in the cold with 6N hydrochloric acid and the oil formed is extracted with methylene chloride. The organic phase is washed to neutrality and then dried.

Yield: 65%

Melting point: 138° C.

NMR spectrum (CDCl$_3$+DMSO—d$_6$): 2.65 to 3.2 ppm, t, 4H; 3.2 ppm, t, 2H; 4.65 ppm, t, 2H; 6.8 ppm, m, 1H; 7.8 ppm, m, 2H; 10.9 ppm 1H, exchangeable.

STAGE B 4-(2,3-Dihydro-5-benzofuranyl)butanoic acid 300 g of zinc and 30 g of mercuric chloride are added with stirring to a mixture containing 510 ml of concentrated hydrochloric acid in 240 ml of water, 141 g of 4-(2,3-dihydro-5-benzofuranyl)-4-oxobutanoic acid obtained above and 300 ml of toluene. The reaction medium is brought to reflux for 6 hours. 150 ml of concentrated hydrochloric acid are added and refluxing is continued overnight.

After cooling, and separation following settling, the toluene phase is exhaustively extracted using 1N sodium hydroxide.

From this aqueous phase, acidified and extracted with methylene chloride, 4-(2,3-dihydro-5-benzofuranyl)-butanoic acid is recovered and recrystallized in isopropyl ether.

Yield: 64%.

Melting point: 84–85° C.

NMR spectrum (CDCl$_3$): 2 ppm, m, 2H; 2.4 to 2.5 ppm, t, 4H; 3.2 ppm, m, 2H; 4.55 ppm, t, 2H; 6.7 ppm, m, 1H; 6.95 ppm, m, 1H; 7.05 ppm, m, 1H; 11.15 ppm, 1H, exchangeable.

STAGE C

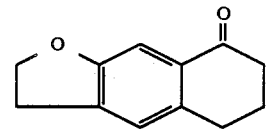

A solution of 86 g of the acid obtained in the preceding stage in 900 ml of xylene is introduced into a mixture, brought to 95°–100° C., of 258 g of polyphosphoric acid and 4.3 liters of xylene.

After 30 minutes at this temperature, the mixture is hydrolyzed with 4.3 liters of water and ice. After extraction, the organic phases are washed with 10% strength sodium bicarbonate solution and then with water saturated with sodium chloride.

After evaporation, the exposed product is obtained and recrystallized in isopropyl ether.

Yield: 58.5%.

Melting point: 67° C.

NMR spectrum (CDCl$_3$): 2.15 ppm, m, 2H; 2.4 and 3.2 ppm, m, 4H; 3.25 ppm, t, 2H; 4.65 ppm, t, 2H; 7.5 and 7.2 ppm, m, 2H.

EXAMPLE 2 dl-7-Amino-2,3,5,6,7,8-hexahydronaphtho[2,3-b]furan hydrochloride

STAGE A 2,3,5,6,7,8-Hexahydronaphtho[2,3-b]furan-8-one oxime

A mixture containing 46 g of the compound of Example 1, 60 g of hydroxylamine hydrochloride and 60 g of anhydrous sodium acetate in 410 ml of ethanol is brought to reflux for 5 hours. The mixture is then cooled and diluted with water, extracted with methylene chloride, dried and evaporated to dryness. The dry residue is recrystallized in ethanol.

Yield: 78%.
Melting point: 165° C.
NMR spectrum (CDCl$_3$): 1.8 ppm,m,2H; 2.5 to 2.9 ppm, m, 4H; 3.15 ppm,t,2H; 4.55 ppm,t,2H; 7 to 7.4 ppm,m,2H; 10.3 ppm,m,1H.

STAGE B 2,3,5,6,7,8-hexahydronaphtho[2,3-b]furan-8-one oxime para-toluenesulfonate A mixture of 35 g of the oxime obtained in the preceding stage and 38 g of para-toluenesulfonyl chloride in 160 ml of pyridine is stirred for 16 hours at a temperature below 5° C.

After dilution in 1 liter of water, the reaction medium is extracted with methylene chloride, dried and evaporated.

Yield: 94%.
Melting point: 141°–143° C.
NMR spectrum (CDCl$_3$): 1.17 ppm,m,2H; 2.4 ppm,s,3H; 2.6 ppm,m,4H; 3.15 ppm,t,2H; 4.5 ppm,t,2H; 6.95 to 7.2 ppm, m,2H; 7.3 ppm,m,2H; 7.9 ppm,m,2H.

STAGE C

7-Acetylamino-2,3,5,6,7,8-hexahydronaphtho[2,3-b]furan-8-one

A suspension of 57 g of the compound obtained in the preceding stage and 340 ml of anhydrous benzene is added in the course of 1 hour to a solution, cooled to 0° C. of sodium ethylate (4.46 g of Na in 140 ml of ethanol). The mixture is stirred for 5 hours at 0° C. and then stored overnight in the ice box.

After the addition of 260 ml of 2N hydrochloric acid, the mixture is filtered. The acid phase is alkalinized and then extracted with methylene chloride. After drying and evaporation, the oil is immediately acetylated with a mixture of 44 ml of acetic acid and 11 ml of acetic anhydride.

The mixture is diluted with water and extracted with methylene chloride and the organic phase is then washed with water. After evaporation, the residue is recrystallized in acetonitrile.

Yield: 7%.
Melting point: 180° C.
NMR spectrum (CDCl$_3$): 2.1 ppm,s,3H; 1.5 to 3.2 ppm,m, 4H; 3.3 ppm,t,2H; 4.6 ppm,m,1H; 4.65 ppm,t,2H; 7.0 ppm, 1H, exchangeable; 7.15 ppm,m,1H.

STAGE D

7-Acetylamino-2,3,5,6,7,8-hexahydronaphtho[2,3-b]furan 2.4 g of the compound obtained in the preceding stage are reduced in a Parr apparatus for 5 hours at room temperature under a hydrogen pressure of 5 kg, in solution in 54 ml of acetic acid and 2 ml of 70% strength perchloric acid in the presence of palladium on charcoal (5% palladium). The reaction medium is then diluted with methylene chloride, and washed with 10% strength sodium bicarbonate solution in water and then with pure water. After evaporation of the solvent and recrystallization in acetonitrile, the pure product is obtained.

Yield: 50%.
Melting point: 185–186° C.
NMR spectrum (CDCl$_3$):L 1.2 to 2.5 ppm,m,5H; 2.5 to 3.3 ppm,m,6H; 3.5 to 4.5 ppm,m,1H; 4.5 ppm,t,2H; 5.5 to 6.1 ppm 1H, exchangeable; 6.5 ppm,s,1H; 7 ppm,s,1H.

STAGE E 1 g of amide obtained in the preceding stage is brought to reflux for 18 hours with 25 ml of 4N hydrochloric acid.

After being cooled, the reaction medium is alkalinized and extracted with methylene chloride. After drying and evaporation, 7-amino-2,3,5,6,7,8-hexahydronaphtho-[2,3-b]furan is obtained.

Melting point: 60° C.

The corresponding hydrochloride is obtained after dissolving the base obtained above in ethyl acetate and adding a sufficient quantity of hydrochloric acid dissolved in ethyl ether.

Overall yield: 55%.
Melting point: 275° C.
The NMR spectrum of this compound is shown in Table I.

EXAMPLE 3 d-7-Amino-2,3,5,6,7,8-hexahydronaphtho[2,3-b]furan hydrochloride

STAGE A d-7-Amino-2,3,5,6,7,8-hexahydronaphtho[2,3-b]furan camphorsulfonate

This salt was obtained by reacting the compound of Example 2 with an equimolar quantity of d-camphorsulfonic acid. After two recrystallizations in ethanol followed by two recrystallizations in methanol, the salt is obtained optically pure.

Melting point: 253°–261° C.
Rotatory power of a 0.5% strength solution in water:

| λ nm | $[\alpha]_D^{23°\ C.}$ |
|------|------------------------|
| 589  | +41.3°                 |
| 578  | +43.3°                 |
| 546  | +51.1°                 |
| 436  | +105.6°                |
| 365  | +235.0°                |

STAGE B

The camphorsulfonate obtained in the preceding stage is dissolved in ethyl acetate and the medium is then alkalinized with sodium hydroxide. The organic phase is separated, dried over anhydrous sodium sulfate and evaporated. The oil obtained is taken up in acetonitrile and a stoichiometric quantity of ethereal hydrogen chloride is then added, to obtain optically pure d-7-amino-2,3,5,6,7,8-hexahydronaphtho[2,3-b]furan hydrochloride.

Melting point: 261°–264° C.
Rotatory power of a 0.25% strength solution in DMSO:

| λ nm | $[\alpha]_D^{23°\ C.}$ |
|------|------------------------|
| 589  | +86.4°                 |
| 578  | +90.4°                 |

-continued

| λ nm | $[\alpha]_D^{23°\,C.}$ |
|---|---|
| 546 | +104.4° |
| 436 | +191.6° |
| 365 | +350.2° |

EXAMPLE 4 l-7-Amino-2,3,5,6,7,8-hexahydronaphtho[2,3-b]furan hydrochloride

This hydrochloride was obtained according to the process described in Example 3, but using l-camphorsulfonic acid in Stage A.

Melting point: 262°-264° C.

Rotatory power of a 0.25% strength solution in DMSO:

| λ nm | $[\alpha]_D^{23°\,C.}$ |
|---|---|
| 589 | −86.4° |
| 578 | −90.4° |
| 546 | −104.4° |
| 436 | −191.6° |
| 365 | −350.2° |

EXAMPLE 5 dl-7-(N,N-Dipropylamino)-2,3,5,6,7,8-hexahydronaphtho-[2,3-b]furan 13.4 g of propyl iodide and 11 g of potassium carbonate are added to 1.5 g of the compound of Example 2 dissolved in 10 ml of acetonitrile.

After 4 days with efficient stirring at room temperature, the mixture is filtered and the solvent concentrated under vacuum. The residue is recrystallized in pentane to give the expected product.

Yield: 45%.

Melting point: 46°-48° C.

The NMR spectrum of the compound is shown in Table I.

EXAMPLE 6 dl-7-(N,N-Dimethylamino)-2,3,5,6,7,8-hexahydronaphtho-[2,3-b]furan hydrochloride 3.35 ml of 37% strength formaldehyde solution in water are added to a solution of 1.1 g of the compound of Example 2 in 2 ml of concentrated formic acid. The mixture is brought for 2 hours to reflux, cooled, diluted with 20% strength sodium hydroxide solution in water and then extracted with methylene chloride. The organic phase is concentrated and a sufficient quantity of ethereal hydrogen chloride is then added. The salt thereby obtained is recrystallized in acetonitrile.

Yield: 64%.

Melting point: 230° C.

The NMR spectrum of dl-7-(N,N-dimethylamino)-2,3,5,6,7,8-hexahydronaphtho[2,3-b]furan in shown in Table I.

EXAMPLE 7 dl-7-(N-Benzylamino)-2,3,5,6,7,8-hexahydronaphtho[2,3-b]-furan 45 g of the compound of Example 2, 25.4 g of benzaldehyde and 300 ml of benzene are brought to reflux, removing the water formed. The mixture is evaporated to dryness, the residue is taken up with 300 ml of ethanol and 9 g of sodium borohydride are added portionwise, keeping the temperature at approximately 18° C. After one night at room temperature, the ethanol is removed under vacuum and the residue taken up with dilute hydrochloric acid solution. The acid phase is alkalinized and then extracted with ethyl ether. After evaporation of the solvent, the oil obtained is purified on a silica column using a mixture of methylene chloride and methanol (95:5 V/V) as elution solvent.

Yield: 37.7%.

The NMR spectrum of this compound is shown in Table I.

EXAMPLE 8 dl-7-(N-Benzyl-N-methylamino)-2,3,5,6,7,8-hexahydronaphtho-[2,3-b]furan 44 ml of 37% strength formaldehyde solution in water are added to a solution of 21 g of the compound of Example 7 in 26 ml of concentrated formic acid maintained at 0° C. After 2 hours under reflux, the cooled reaction medium is diluted with 40% strength sodium hydroxide solution in water and extracted with methylene chloride. The organic phase is washed, dried and then evaporated under vacuum. The residue, purified by passage through a silica column, leads to the production of an oil. The elution solvent used is a mixture of methylene chloride and ethyl acetate (85:15 V/V)

Yield: 33.3%.

The NMR spectrum of the compound is shown in Table I.

EXAMPLE 9 dl-7-(N-Methylamino)-2,3,5,6,7,8-hexahydronaphtho[2,3-b]-furan hydrochloride 7 g of the compound of Example 8 in 240 ml of ethanol are introduced into a Parr apparatus under a hydrogen pressure of 5 kg/cm$^2$, at room temperature, with 0.5 g of palladium on charcoal (5% palladium). After filtration of the catalyst and evaporation of the solvent, the crude base is obtained. The hydrochloride is formed after diluting the base in ethyl acetate and adding ethereal hydrogen chloride.

Yield: 67%.

Melting point: 231°-234° C.

The NMR spectrum of this compound is shown in Table I.

EXAMPLE 10 dl-7-(N-Cyclohexylmethyl-N-methylamino)-2,3,5,6,7,8-hexahydronaphtho[2,3-b]furan hydrochloride

STAGE A 7-(N-Benzylimino)-2,3,5,6,7,8-hexahydronaphtho[2,3-b]furan 10 g of the compound of Example 2 are brought to reflux in 200 ml of ethanol in the presence of 2.8 g of benzaldehyde. A sample is removed, concentrated and recrystallized in ethanol.

Melting point: 122° C.

NMR spectrum (CDCl$_3$): 1.5 to 2.3 ppm,m,2H; 2.7 to 3.3 ppm,m,4H; 3 to 3.4 ppm,t,2H; 3.3 to 3.9 ppm,m,1H; 4.55 ppm, t,2H; 6.6 ppm,s,1H; 7 ppm,s,1H; 7.3 to 7.6 ppm,m,3H; 7.6 to 8 ppm,m,2H; 8.5 ppm,s,1H.

STAGE B

The imine obtained in the preceding stage is then hydrogenated in the presence of 0.3 g of platinum (IV) oxide under a hydrogen pressure of 10 kg/cm$^2$ for 4 hours at 70° C. After filtration of the catalyst and evaporation of the solvent under vacuum, 9 g of an oil containing a mixture of derivatives of benzene and of cyclohexane are obtained.

This mixture is then treated without further processing with 9.9 ml of formic acid at 0° C., and then with 16.7 ml of 37% strength formaldehyde solution in water. After being heated for 2 hours under reflux, the mixture is neutralized with 20% strength sodium hydroxide solution in water and extracted with methylene chloride, and the extract is washed with water. The solvent is evaporated off under vacuum to obtain an oil which is purified on a silica column, using a mixture of methylene chloride and ethyl acetate as eluant. dl-7-(N-Cyclohexylmethyl-N-methylamino)-2,3,5,6,7,8-hexahydronaphtho[2,3-b]furan is obtained. After dilution of the latter compound in acetonitrile and addition of ethereal hydrogen chloride, dl-7-(N-cyclohexylmethyl-N-methylamino)-2,3,5,6,7,8-hexahydronaphtho[2,3-b]furan hydrochloride is obtained.

Yield: 6.5%.

The NMR spectrum of this compound is shown in Table I.

EXAMPLE 11

Ethyl dl-7-{N-(2,3,5,6,7,8-hexahydronaphtho[2,3-b]furan-7-yl)amino}heptanoate

A mixture of 5.5 g of the compound of Example 2, 7.11 g of ethyl 7-bromoheptanoate and 4.25 g of sodium carbonate dissolved in 35 ml of ethanol are brought to reflux for 20 hours. After dilution with 20 ml of 1N sodium hydroxide, the mixture is extracted with ethyl acetate, the extract washed with water and dried and the solvent evaporated off under vacuum. The residue is taken up with stirring with a stoichiometric quantity of 1N hydrochloric acid, until crystallization is complete. After filtration and drying, the hydrochloride is collected.

Yield: 50%.

Melting point: 161°–166° C.

The NMR spectrum of this compound is shown in Table I.

EXAMPLE 12 dl-7-{N-(2,3,5,6,7,8-Hexahydronaphtho[2,3-b]furan-7-yl)-amino}heptanoic acid hydrochloride A solution of 1.4 g of potassium hydroxide in 10 ml of water is added to a suspension of 4.7 g of the compound of Example 11, in hydrochloride form, in ethanol. After 24 hours at room temperature, a quantity of the potassium hydroxide solution is added again and the mixture is stirred for 2 hours at room temperature. The ethanol is evaporated off under vacuum without heating. The residue is taken up with 1N hydrochloric acid and then recrystallized in water.

Yield: 62%.

Melting point: 197°–200° C.

The NMR spectrum of this compound is shown in Table I.

EXAMPLE 13 dl-7-[N-(2-Ethoxyethyl)amino]-2,3,5,6,7,8-hexahydronaphtho-[2,3-b]furan

A mixture containing 7.8 g of the compound of Example 2, 6.7 g of 2-bromoethyl ethyl ether and 6.2 g of sodium carbonate in ethanol is brought to reflux with stirring for 20 hours.

After filtration and washing of the residue with ethanol, the ethanol phases are evaporated off. The residual oil is taken up with water and ether and, after separation following settling, the ether phase is exhaustively extracted with 1N hydrochloric acid. The acid aqueous phase, alkalinized in the cold, extracted with ether, dried and then evaporated, yields an oil having the expected structure.

Yield: 44%.

The NMR spectrum of this compound is shown in Table I.

The oil obtained above, dissolved in ethanol and after acidification with ethereal hydrogen chloride, gives the corresponding hydrochloride.

Melting point: 180°–181° C.

EXAMPLE 14 dl-7-[N-(2-Hydroxyethyl)amino]-2,3,5,6,7,8-hexahydronaphtho[2,3-b]furan 7.7 g of 7-amino-2,3,5,6,7,8-hexahydronaphtho-[2,3-b]furan, 5 g of bromoethanol, 40 ml of methylene chloride, 12 ml of 40% strength sodium hydroxide in water and 1 g of Triton B are stirred vigorously at room temperature for 48 hours. After separation following settling, the methylene chloride is evaporated off in the cold and the residue is taken up with ethyl ether, which is exhaustively extracted with hydrochloric acid. The alkalinized acid phases yield an oil having the expected structure.

Yield: 71%.

The NMR spectrum of this compound is shown in Table I.

EXAMPLE 15 dl-8-Amino-2,3,5,6,7,8-hexahydronaphtho[2,3-b]furan hydrochloride

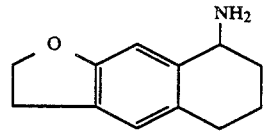

2 g of oxime obtained in Stage A of Example 2, in 200 ml of ethanol, are introduced into a Parr apparatus under a hydrogen pressure of 5 kg/cm² with 0.5 g of palladium on charcoal (5% palladium) for 5 hours. After filtration of the catalyst and evaporation of the solvent under vacuum, 1.7 g of crude base are obtained. The hydrochloride is obtained in ethyl acetate after adding ethereal hydrogen chloride.

Yield: 53.3%.

Melting point: >260° C.

NMR spectrum (D$_2$O): 1.85 ppm,m,4H; 2.6 ppm,t,2H; 4.35 ppm,m,1H; 3 ppm,t,2H; 4.4 ppm,t,2H; 6.7 to 7 ppm,m,2H

EXAMPLE 16

2,3,5,6,7,8-Hexahydronaphtho[2,3-b]furan

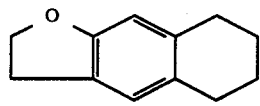

An amalgam of zinc and mercuric chloride (72 g Zn and 7.1 g HgCL$_2$) is added to a mixture containing 120 ml of concentrated hydrochloric acid, 57 ml of water, 30 g of the compound of Example 1 and 71 ml of toluene, with stirring.

The reaction medium is brought to reflux for 4 hours. After cooling, and separation following settling, the toluene phase is washed with sodium bicarbonate solution and then with saturated sodium chloride solution. The organic phase is dried and then concentrated under vacuum, and the residue is distilled under vacuum to obtain the expected compound.

Yield: 59%.

NMR spectrum (CDCl$_3$); 1.7 ppm,m,4H; 2.65 ppm,m,4H; 3.05 ppm,t,2H; 4.45 ppm,t,2H; 6.5 ppm,m,1H; 6.9 ppm,m,1H.

EXAMPLE 17

2,3,5,6,7,8-Hexahydronaphtho[2,3-b]furan-5-one

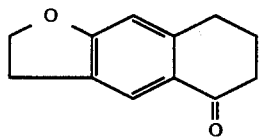

30 g of the compound of Example 16 are dissolved in 130 ml of acetic acid and 32 ml of propionic acid, and then cooled to between 0° and 5° C. A solution of Jones's reagent is added, the temperature being maintained at approximately 5° C. The mixture, maintained for one hour at this temperature, is concentrated under vacuum and then taken up with sodium bicarbonate solution in the presence of ether. After filtration, the ether phase is decanted and washed with saturated sodium chloride solution to obtain, after evaporation and drying, an oil which crystallizes.

Yield: 56%.

Melting point: 78° C.

NMR spectrum (CDCl$_3$): 2.1 ppm,m,2H; 2.6 ppm,t,2H; 2.9 ppm,t,2H; 3.2 ppm,t,2H: 4.65 ppm,t,2H; 6.6 ppm,m,1H; 7.9 ppm,m,1H.

EXAMPLE 18 dl-5-Amino-2,3,5,6,7,8-hexahydronaphtho[2,3-b]furan hydrochloride

STAGE A 2,3,5,6,7,8-Hexahydronaphtho[2,3-b]furan-5-one omixe 18 g of the compound of Example 17, 23.5 g of hydroxylamine hydrochloride and 23.5 g of sodium acetate in 160 ml of ethanol are brought to reflux for 2 hours. The mixture is then cooled, diluted with water and then extracted with methylene chloride. After the organic phase has been dried over anhydrous magnesium sulfate and evaporated to dryness, the oxime is obtained after recrystallization in ethanol.

Yield: 60.7%.

Melting point: 155°–156° C.

NMR spectrum (CDCl$_3$): 1.75 ppm,m,2H; 2.6 ppm,m,4H; 3.1 ppm,t,2H; 4.5 ppm,t,2H; 6.5 ppm,m,1H; 7.7 ppm,m,1H; 8.3 ppm, 1H, exchangeable.

STAGE B

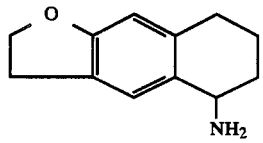

5 g of oxime obtained in the preceding stage, in 750 ml of ethanol, are introduced into a Parr apparatus under a hydrogen pressure of 5 kg/cm$^2$ with 2 g of palladium on charcoal (5% palladium) for approximately 2 hours 30 minutes. After filtration of the catalyst and evaporation of the solvent, 4.5 g of crude base are obtained. The hydrochloride is obtained after dissolving the base in ethyl acetate and adding ethereal hydrogen chloride.

Yield: 36%.

Melting point: 208° C.

NMR spectrum (D$_2$O): 1.9 ppm,t,4H; 2.65 ppm,t,2H; 3.1 ppm,t,2H; 4 to 4.5 ppm,m,3H; 6.6 ppm,m,1H; 7.2 ppm,m, 1H.

EXAMPLE 19 dl-6-Amino-2,3,5,6,7,8-hexahydronaphtho[2,3-b]furan hydrochloride

STAGE A

6-Bromo-2,3,5,6,7,8-hexahydronaphtho[2,3-b]furan-5-one 55.33 g of pyridinium bromide perbromide are added portionwise at 0° C. to a solution of 27.1 g of 2,3,5,6,7,8-hexahydronaphtho[2,3-b]furan-5-one, the compound of Example 17, in 1.5 of chloroform. The mixture is left overnight at room temperature. The reaction mixture is then washed with water and the organic phase dried over anhydrous magnesium sulfate. Evaporation of the chloroform yields 39.85 g of a mixture which is then purified on a silica column using a mixture of methylene chloride and cyclohexane (80:20 V/V) as solvent. The product obtained is then recrystallized in ethyl acetate.

Yield: 48%.

Melting point: 106° C.

NMR spectrum (CDCl$_3$): 3.2 ppm,m,4H; 3.2 ppm,t,2H; 4.5 to 4.8 ppm,m,3H; 6.65 ppm,s,1H; 8 ppm,s,1H.

STAGE B

6-Azido-2,3,5,6,7,8-hexahydronaphtho[2,3-b]furan-5-one

A solution of 4.50 g of sodium azide in 65 ml of distilled water is added dropwise at 0° C. to a solution of 18.4 g of the compound obtained in the preceding stage in 535 ml of dimethylformamide and 13 ml of acetic acid. The reaction mixture is stored overnight at −18° C., and it is then diluted with water and taken up with dichloromethane. The organic phase is dried and evaporated to obtain 19 g of the expected product.

STAGE C

6-Azido-5-hydroxy-2,3,5,6,7,8-hexahydronaphtho[2,3-b]furan 19 g of the compound obtained in the preceding stage are dissolved in anhydrous ethanol. 1.3 g of sodium borohydride are added to this solution. After 1 hour at room temperature, the reaction mixture is concentrated under vacuum, taken up with water and extracted with methylene chloride. The organic phase is dried over anhydrous magnesium sulfate and evaporated. 9.8 g of 6-azido-5-hydroxy-2,3,5,6,7,8,-hexahydronaphtho[2,3-b]furan are obtained, which are used in the following stage without further purification.

STAGE D

6-Azido-2,3,5,6,7,8-hexahydronaphtho[2,3,-b]furan

The compound obtained in the preceding stage is dissolved in 288 ml of triethylsilane and 288 ml of carbon tetrachloride. 144 ml of trifluoroacetic acid are added dropwise under nitrogen. The reaction mixture is left for 36 hours at room temperature and then poured onto ice, and settling is allowed to occur. The organic phase is washed with 1N sodium hydroxide, dried over magnesium sulfate and then evaporated. 5.9 g of 6-azido-2,3,5,6,7,8-hexahydronaphtho[2,3-b]furan are obtained, and used immediately in the next stage.

STAGE E

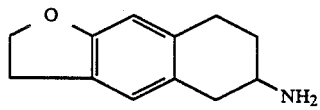

The compound obtained in the preceding stage is dissolved in 400 ml of a mixture of ethanol and anhydrous tetrahydrofuran (V/V), containing 10 ml of Raney nickel. 4 ml of hydrazine hydrate diluted in 20 ml of ethanol are then added dropwise. The reaction mixture is left overnight at room temperature and then evaporated to dryness, the residue is taken up with methylene chloride and the mixture is filtered. The filtrate is dried and then evaporated. The amine hydrochloride is formed by dissolving the evaporation residue in ethanol and adding ethereal hydrogen chloride. The solution is evaporated to dryness. The hydrochloride is recrystallized in methanol. Melting point: 241°-243° C.

NMR spectrum (D$_2$O=1 drop DCl): 1.5 to 2.5 ppm,m,2H; 2.5 to 3.7 ppm,m,1H=t,2H,=m,4H; 4.4 ppm,t,2H; 6.6 ppm, s,1H; 7.1 ppm,s,1H.

EXAMPLE 20 dl-6-Amino-6-methyl-2,3,5,6,7,8-hexahydronaphtho[2,3-b]furan hydrochloride

STAGE A 6,6-Dibromo-2,3,5,6,7,8-hexahydronaphtho[2,3-b]furan-5-one 24.44 g of pyridinium bromide perbromide are added portionwise to a solution of 6.21 g of the compound of Example 17 in 350 ml of chloroform. After 10 hours' contact, the reaction mixture is poured onto ice, settling is allowed to occur and the organic phase is washed with 0.1N sodium thiosulfate and then with water, and thereafter dried and evaporated. The residue is recrystallized in ethyl acetate to obtain pure 6,6-dibromo-2,-3,5,6,7,8-hexahydronaphtho[2,3-b]furan-5-one.

Yield: 61%.

Melting point: 138°-142° C.

NMR spectrum (DMSO-d$_6$): 3 ppm,s,4H; 3 to 3.4 ppm,t,2H; 4.5 to 4.8 ppm,t,2H; 6.65 ppm,s,1H; 7.9 ppm,s,1H.

STAGE B

6-Bromo-6-methyl-2,3,5,6,7,8-hexahydro[2,3-b]furan-5-one 42 ml of 2N methylmagnesium iodide are added rapidly at −40° C. to a solution of 5.94 g of copper (I) bromide in 120 ml of anhydrous tetrahydrofuran. The temperature is allowed to rise to 0° C. and, after 45 minutes, the temperature of the medium is brought to −60° C. and 6.92 g of the compound obtained in the preceding stage are added rapidly. After 10 minutes' contact at −60° C., the temperature of the medium is raised to approximately 20° C. and 5 ml of methylene iodide are added. The reaction medium is left to stand at 20° C. and the mixture is then hydrolyzed at −60° C. with 80 ml of 4N sulfuric acid. The reaction medium is extracted with pentane and the organic phase is then dried and evaporated. After recrystallization in isopropyl ether, pure 6-bromo-6-methyl-2,3,5,6,7,8-hexahydronaphtho[2,3-b]furan-5-one is obtained.

Yield: 12%.

Melting point: 95°-98° C.

NMR spectrum (CDCl$_3$): 2 ppm,s,3H; 1.9 to 3.2 ppm,m,4H: 3.2 ppm,t,2H; 4.7 ppm,t,2H; 6.6 ppm,s,1H; 2 ppm,s,1H.

STAGE C

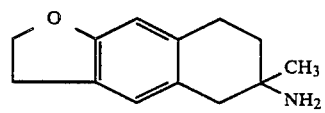

This compound was obtained from 6-bromo-6-methyl-2,3,5,6,7,8-hexahydronaphtho[2,3-b]furan-5-one and according the processes described in Example 19, Stages B, C, D and E. D and E.

EXAMPLE 21 dl-7-Amino-5,6,7,8-tetrahydronaphtho[2,3-furan hydrochloride

STAGE A

7-Methoxy-1,2,3,4-tetrahydro-2-naphthalenone 46.84 g (0.249 mol) of 2,7-dimethoxynaphthalene are suspended in 508 ml of anhydrous methanol. 48.7 g of sodium metal are added as rapidly as possible, and the mixture is then heated until dissolution of the sodium is complete. After cautious hydrolysis with 425 ml of water, 468 ml of concentrated hydrochloric acid are added as rapidly as possible, with cooling. The formation of a precipitate is observed. The mixture is brought to reflux for approximately 2 hours. The mixture is allowed to cool and then extracted with 1,200 ml of ethyl ether, and the organic phase is washed to neutrality with water and dried over magnesium sulfate.

The oil obtained is taken up, with stirring, with 53 ml of a 50% strength sodium hydrosulfite solution and 30 ml of water. After 30 minutes' contact, the addition of water brings about the formation of a precipitate. The latter is filtered off. The residue is washed with ethyl ether and then taken up in 250 ml of 10% strength sodium carbonate and 100 ml of ethyl ether. The two phases are shaken until the mixture is clear to obtain 20.2 g of expected product.

STAGE B

7-Methoxy-1,2,3,4-tetrahydro-2-naphthalenone oxime 4.12 g of the compound obtained in the preceding stage are dissolved in 40 ml of ethanol in the presence of 6.27 g of hydroxylamine hydrochloride and 5.8 g of sodium acetate. The reaction mixture is brought for 5 hours to reflux and then poured into 100 ml of water, and this mixture is then extracted with 240 ml of methylene chloride. The organic phase is washed with saturated sodium chloride solution and dried over anhydrous magnesium sulfate. After evaporation of the solvent, the residue obtained is recrystallized in 30 ml of isopropyl ether to obtain the pure extracted compound.

Yield: 42%.
Melting point: 120°–122° C.
NMR spectrum (CDCl$_3$): 2.5 to 3 ppm,m,4H; 3.5 ppm,s,2H; 3.8 ppm,s,3H; 6.6 to 7.3 ppm,m,3H; 8.1 ppm,1H, exchangeable.

STAGE C

2-Amino-7-methoxy-1,2,3,4,-tetrahydronaphthalene 2 g of the compound obtained in the preceding stage, dissolved in 50 ml of ethanol, are hydrogenated in the presence of 5 ml of Raney nickel and 2 ml of ammonia solution. After absorption of the theoretical quantity of hydrogen, the ethanol is evaporated off, the residue taken up with 50 ml of methylene chloride and the mixture extracted with 4 times 40 ml of 1N hydrochloric acid. The acid aqueous phase is alkalinized using 1N sodium hydroxide and extracted with methylene chloride, the extract is washed to neutrality, dried over anhydrous magnesium sulfate and evaporated to obtain 1.1 g of an oil whose structure corresponds to that of the expected amine.

Yield: 64%.
NMR spectrum (CDCl$_3$): 1.4 ppm, 2H, exchangeable; 1.5 to 3.4 ppm,m,7H; 3.8 ppm,s,3H; 6.6 to 6.9 ppm,m,2H; 7.1 ppm,d,1H.

STAGE D

2-Acetamido-7-methoxy-1,2,3,4-tetrahydronaphthalene

The total quantity obtained in the preceding stage is treated with 1 ml of acetic anhydride in the presence of 10 ml of acetic acid. After approximately 3 hours' contact, the mixture is taken up with 50 ml of water and 50 ml of 1N hydrochloric acid and extracted with methylene chloride, and the extract is washed to neutrality and dried over anhydrous magnesium sulfate. After evaporation of the solvent, the expected amide is obtained.

Yield: 63%.
Melting point: 106°–108° C.
NMR spectrum (CDCl$_3$): 1.9 ppm,s,3H; 1.3 to 2.1 ppm,m,2H; 2.2 to 3.3 ppm,m,4H; 3.7 ppm,s,3H; 4.2 ppm,m,1H; 5.4 to 6 ppm, 1H, exchangeable; 6.3 to 7.2 ppm,m,3H.

STAGE E

2-Acetamido-7-hydroxy-1,2,3,4-tetrahydronaphthalene 6 g of the compound obtained in the preceding stage are dissolved in 80 ml of anhydrous chloroform, and 5.17 ml of boron tribromide are then added dropwise. The reactants are left in contact for 2 hours at room temperature. The mixture is treated with 15 ml of anhydrous ethanol to bring about the formation of a precipitate which, after filtration, is stirred in 100 ml of water. The water is decanted and the remaining precipitate washed until bromide ions are absent, to obtain the pure amide.

Yield: 86%.
Melting point: 199° C.
NMR spectrum (DMSO-d$_6$): 1.1 to 1.2 ppm,m,2H; 1.8 ppm,s,3H; 2.3 to 2.9 ppm,4,4H; 3.5 to 4.2 ppm,m,1H; 6.3 to 6.7 ppm,m,2H; 6.9 ppm,d,1H; 7.2 to 8.5 ppm,2H, exchangeable.

STAGE F

2-Acetamido-6-(2-chloro-1-oxoethyl)-7-hydroxy-1,2,3,4,-tetrahydronaphthalene 5 g of the phenol obtained in the preceding stage, suspended in methylene chloride, are added to 58 ml of a molar solution of boron trichloride in methylene chloride. 4.4 g of chloroacetonitrile are then added followed, portionwise, by 3.69 g of aluminum chloride, the temperature being maintained in the region of 0° C. The mixture is left stirred for 4 hours at 0° C. and then left overnight at room temperature, and it is then hydrolyzed with 15 ml of water and 27 ml of 10% strength aqueous hydrochloric acid solution. This mixture is left for 1 hour with stirring and then alkalinized with 20% strength ammonia solution in water. The precipitate obtained is filtered off on celite, followed by washing with methylene chloride, the two phases are separated after settling has occurred and the organic phase is dried over anhydrous magnesium sulfate. After evaporation of the solvent, the residue is recrystallized in ethanol.

Yield: 52%.
Melting point: 166° C.
NMR spectrum (DMSO-d$_6$): 1.3 to 2.3 ppm,m,2H; 1.9 ppm, s,3H; 2.4 to 3.2 ppm,m,4H; 3.5 to 4.2 ppm,m,1H; 5.1 ppm, s,2H; 6.8 ppm,s,1H; 7.7 ppm,s,1H; 8 ppm, 1H, exchangeable; 10.9 ppm, 1H, exchangeable.

STAGE G

7-Acetamido-2,3,5,6,7,8-hexahydronaphtho[2,3-b]furan-3-one

A mixture of 3.5 g of the compound obtained in the preceding stage, 9 ml of triethylamine and 70 ml of chloroform is brought for 2 hours to reflux. The mixture is evaporated to dryness and the residue taken up with 100 ml of water, and the expected product is precipitated with ether. The precipitate is filtered off and washed several times with water until chloride ions are absent, to obtain the pure amide after drying.

Yield: 92%.
Melting point: 191° C.
NMR spectrum (CDCl$_3$=DMSO—d$_6$): 1.4 to 2.5 ppm,m,2H; 2 ppm,s,3H; 2.5 to 3.5 ppm,m,4H; 3.9 to 4.6 ppm,m,1H; 4.6 ppm,s,2H; 6.7 ppm, 1H, exchangeable; 6.9 ppm,s,1H; 7.4 ppm,s,1H.

STAGE H

7-Acetamido-3-hydroxy-2,3,5,6,7,8-hexahydronaphtho[2,3-b]-furan 2.8 g of the ketone obtained above are suspended in 27 ml of methanol and 13.5 ml of 10% strength sodium bicarbonate solution. 0.87 g of sodium borohydride is added portionwise, the temperature being maintained at 18° C. The reaction medium is left overnight at room temperature. It is hydrolyzed with 300 ml of water and 70 ml of hydrochloric acid. The aqueous phase, saturated with sodium chloride, is extracted with methylene chloride to give the expected product.

Yield: 37%.

Melting point: 254° C.

NMR spectrum (CDCl3): 1.1 to 2.4 ppm,m,2H; 2 ppm,s3H; 2.5 to 3.3 ppm,m,4H; 3.8 to 4.4 ppm,m,1H; 4.4 ppm,m,2H; 4.6 ppm,1H, exchangeable; 4.5 to 4.9 ppm,m,1H; 6.5 ppm,s,1H; 6.3 to 7 ppm, 1H, exchangeable; 7.1 ppm,s,1H.

STAGE I

7-Acetamido-5,6,7,8-tetrahydronaphtho[2,3-b]furan 1 g of the compound obtained in the preceding stage is suspended in 7.4 ml of 10% strength hydrochloric acid in water. After 2 hours at room temperature, the mixture is taken up with 100 ml of methylene chloride; the organic phase is washed with water and dried over anhydrous magnesium sulfate. After evaporation of the solvent, the expected amide is obtained.

Yield: 81%.

Melting point: 154° C.

NMR spectrum (CDCl3): 1.5 to 2.5 ppm,m,2H; 2 ppm,s,3H; 2.7 to 3.4 ppm,m,4H; 4.1 to 4.7 ppm,m,1H; 5.4 to 6.1 ppm, 1H, exchangeable; 6.8 ppm,d,1H; 7,3 ppm,s,1H; 7.4 ppm,s,1H; 7.65 ppm,d,1H.

STAGE J

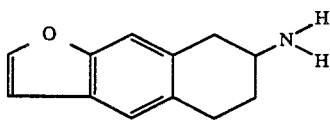

0.55 g of the compound from the preceding stage is dissolved in a mixture of 10 ml of methanol, 1 ml of water and 0.67 g of potassium hydroxide. The mixture is brought to reflux overnight, and then for a further 6 hours after the addition of 0.2 g of potassium hydroxide in 2 ml of methanol and 1 ml of water. The solvent is evaporated off, the residue taken up with methylene chloride, and the mixture is exhaustively extracted with 1N hydrochloric acid. The acid phases are realkalinized with 1N sodium hydroxide and extracted with methylene chloride. After evaporation of the solvent, 7-amino-5,6,7,8-tetrahydronaphtho[2,3-b]furan is obtained.

NMR spectrum (CDCl3): 1.2 to 2.5 ppm,m,2H = exchangeable 2H; 2.5 to 3.4 ppm,m,5H; 6.6 ppm,d,1H; 7.2 ppm,s,1H; 7.3 ppm,s,1H; 7.5 ppm,d,1H.

After addition of the necessary quantity of ethereal hydrogen chloride, the corresponding hydrochloride is obtained.

Melting point: 253°–255° C.

EXAMPLE 22 dl-7-Amino-2,3,5,6,7,8-hexahydronaphtho[2,3-b]furan-3-one hydrochloride

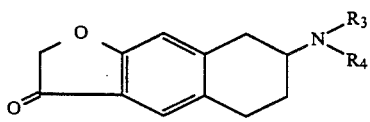

This compound was obtained from 7-acetamido-2,3,-5,6,7,8-hexahydronaphtho[2,3-b]furan-3-one according to the process described in Stage J of the preceding example. NMR spectrum of the corresponding base (CDCl3=1 drop DMSO-d6): 1.25 to 2.65 ppm, 2H, exchangeable; 1.3 to 2.5,m,2H; 2.3 to 3.3 ppm,m,5H; 4.55 ppm,s,2H; 6.8 ppm,s, 1H; 7.3 ppm,s,1H.

EXAMPLE 23 dl-7-Amino-3-hydroxy--2,3,5,6,7,8-hexahydronaphtho[2,3-b]-furan hydrochloride

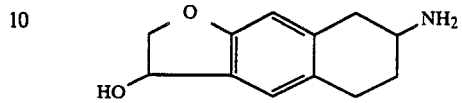

This compound was obtained from 7-acetamido-3-hydroxy-2,3,5,6,7,8-hexahydronaphtho[2,3-b]furan according to the process described in Stage J of Example 21. NMR spectrum of the corresponding base (CDCl3): 0.95 to 2.3 ppm,m,2H; 1.3 to 2.4 ppm, 2H, exchangeable; 2.4 to 3.45 ppm,m,5H; 4.3 ppm,m,2H; 4.6 ppm, 1H, exchangeable; 4.4 to 4.9 ppm,m,1H; 6.5 ppm,s,1H; 7.2 ppm,s,1H.

EXAMPLE 24

Ethyl dl-6-{N-(2,3,5,6,7,8-hexahydronaphtho[2,3-b]furan-7-yl)amino}hexanoate hydrochloride A mixture of 7.7 g of the compound of Example 2, 8.9 g of ethyl 6-bromohexanoate, 9 g of sodium carbonate and 0.1 g of potassium iodide in 50 ml of ethanol is brought to reflux under nitrogen for 24 hours. After being cooled, the mixture is filtered and evaporated under vacuum, and the residue is then taken up with 1N hydrochloric acid in the presence of ether. After filtration and crystallization in water, 9.5 g of hydrochloride are obtained.

Yield: 64%.

Melting point: 166°–168° C.

The NMR spectrum of this compound is shown in Table I.

EXAMPLE 25 dl-6-{-(2,3,5,6,7,8-Hexahydronaphtho[2,3-b]furan-7-yl)-amino}hexanoic acid hydrochloride 7.9 g of the compound of Example 24 are stirred for 3 hours at room temperature in the presence of 45 ml of 1N sodium hydroxide and 45 ml of ethanol. After evaporation of the alcohol under vacuum, 45 ml of hydrochloric acid are added. The hydrochloride obtained is filtered off and recrystallized in water.

Yield: 46%.

Melting point: 203°–204° C.

The NMR spectrum of this compound is shown in Table I.

EXAMPLE 26

Ethyl dl-5-{N-(2,3,5,6,7,8-hexahydronaphtho[2,3-b]furan-7-yl)amino}-5-methylpentanoate hydrochloride A mixture of 7 g of the hydrochloride of Example 2, 7 g of ethyl 5-bromohexanoate (J.A.C.S., 55, 806, 1933) and 7 g of sodium carbonate in 40 ml of ethanol is brought to reflux and with stirring for 20 hours. After evaporation of the ethanol under vacuum, the medium is taken up with ethyl ether and extracted with 1N hydrochloric acid. The aqueous phases are then alkalinized and extracted with ether and the extract is dried over anhydrous sodium sulfate. After evaporation to dryness, 3.2 g of product are obtained.

Yield: 31%.
Melting point: 194° C.
The NMR spectrum of this compound is shown in Table I.

EXAMPLE 27 dl-5-{N-(2,3,5,6,7,8-Hexahydronaphtho[2,3-b]furan-7-yl)-amino}pentanoic acid 4.5 g of ester described in Example 26 are stirred overnight with 14 ml of 1N sodium hydroxide and the necessary quantity of ethanol for homogenizing the mixture. After evaporation, the stoichiometric quantity of hydrochloric acid is added and the acid is crystallized.

Yield: 58.5%.
Melting point: 190°-192° C.
The NMR spectrum of this compound is shown in Table I.

EXAMPLE 28

Ethyl dl-6-{N-(2,3,5,6,7,8-hexahydronaptho[2,3-b]furan-7-yl)amino}-6-methylhexanoate hydrochloride A mixture of 10 g of the compound of Example 2, 12.5 g of ethyl 6-bromoheptanoate (J.A.C.S., 55, 806, 1933), 16.5 g of anhydrous potassium carbonate and 0.1 g of sodium iodide in 100 ml of acetonitrile is brought to reflux for 24 hours. After a further addition of 8.2 g of potassium carbonate, refluxing is continued for 48 hours. The mixture is then cooled, filtered and evaporated to dryness and the residue taken up with ethyl ether in the presence of 1N hydrochloric acid. 10 g of hydrochloride are obtained.

Yield: 55%.
Melting point: 175°-180° C.
NMR spectrum of the compound is shown in Table I.

EXAMPLE 29 dl-6-{N-(2,3,5,6,7,8-Hexahydronaphtho[2,3-b]furan7-yl)-amino}-6-methylhexanoic acid hydrochloride 10 g of the compound of Example 28 are stirred for 3 hours at room temperature in the presence of 60 ml of 1N sodium hydroxide and 60 ml of ethanol. After evaporation of the reaction medium, 60 ml of 1N hydrochloric acid are added. The hydrochloride obtained after filtration is recrystallized in water.

Yield: 42%.
Melting point: 231°-232° C.

EXAMPLE 30

Ethyl dl-7-{N-(2,3,5,6,7,8-hexahydronaphtho [2,3-b]furan-7-yl)amino}7-methylheptanoate hydrochloride This compound was prepared according to the process described in Example 28, but using ethyl 7-bromooctanoate (J.A.C.S., 55, 806, 1933) instead of ethyl 6-bromoheptanoate.

Yield: 33%.
Melting point: 260° C.
The NMR spectrum of this compound is shown in Table I.

EXAMPLE 31 dl-7-{N-(2,3,5,6,7,8-hexahydronaphtho [2,3-b]furan-7-yl)-amino}-7-methylheptanoic acid hydrochloride This compound was prepared from the ester obtained in Example 30 and according to the process described in Example 29.

Yield: 46%.
Melting point: 220° C.
The NMR spectrum of this compound is shown in Table I.

EXAMPLE 32 di-7-[N-(6-Hydroxyhexyl)amino]-2,3,5,6,7,8-hexahydronaphtho[2,3-b]furan hydrochloride 8.3 g of N-{2,3,5,6,7,8-hexahydronaphtho[2,3-b]furan-7-yl}-6-aminohexanoic acid ethyl ester in 80 ml of anhydrous ethyl ether and 30 ml of tetrahydrofuran are added to a suspension of 1 g of lithium aluminum hydride in 30 ml of anhydrous ethyl ether. The reaction medium is brought to reflux for 4 hours. After being cooled, it is then hydrolyzed with 0.7 ml of water, 0.55 ml of 20% strength sodium hydroxide and thereafter 2.5 ml of water. The precipitate is filtered off and the filitrate evaporated to dryness. The dry residue is taken up with isopropanol and a stoichiometric quantity of ethereal hydrogen chloride is added. The precipitate obtained is filtered off and rinsed with a few milliliters of ice-cold ethanol.

Yield: 31%.
Melting poing: 182°-184° C.
The NMR spectrum of this hydrochloride is shown in Table I.

EXAMPLE 33 dl-7-(N-allylamino)-2,3,5,6,7,8-hexahydronaphtho[2,3-b]-furan hydrochloride 5.2 g of 7-amino-2,3,5,6,7,8-hexahydronaphtho[2,3-b]furan dissolved in 27.6 ml of methylene choride are stirred at room temperature in the presence of 8.3 ml of 40% strength sodium hydroxide, 3.3 g of allyl bromide and 1 ml of 40% strength Triton B in methanol. After 20 hours' stirring, 1 ml of Triton B is added again, followed by a further 2 ml after 24 hours' stirring. After 96 hours' stirring, the mixture is separated off after being left of settle and evaporated under vacuum. The residue, taken up in ethyl ether, is washed with water and then dried over anhydrous sodium sulfate. After evaporation, 4.6 g of base are obtained. The corresponding hydrochloride is obtained in acetonitrile by adding a stoichiometric quantity of ethereal hydrogen chloride, and then recrystallized in water.

Yield: 26%.
Melting point: >260° C.
The NMR spectrum of the hydrochloride is shown in Table I.

EXAMPLE 34 dl-7-(N-n-Propylamino)-2,3,5,6,7,8-hexahydronaphtho[2,3-b]furan hydrochloride

STAGE A dl-7-(N-Propionylamino)-2,3,5,6,7,8-hexahydronaphtho[2,3-b]furan

A solution of propionyl chloride in 50 ml of benzene is added dropwise to a solution of 5 g of the compound of Example 2 in 100 ml of benzene and 4.2 ml of triethylamine. After one and a half hours' refluxing, the cooled mixture is diluted with water, separated off after being left to settle and extracted with benzene, and the organic phase is washed with water, dried over anhydrous sodium sulfate and evaporated under vacuum. The dry residue is recrystallized in acetonitrile.

Yield: 38%.

Melting point: 125°-126° C.

NMR spectrum (CDCl$_3$): 1.2 ppm,t,3H; 1.5 to 3.4 ppm,m, =q=m=t,2=2=4=2H; 3.8 to 4.7 ppm,m,1H; 4.5 ppm,t,2H; 5.3 to 5.9 ppm,1H, exchangeable; 6.5 ppm,s,1H; 6.9 ppm,s,1H.

STAGE B 2.3 g of the compound obtained in Stage A in 75 ml of tetrahydrofuran is added under nitrogen to a suspension of 0.36 g of lithium aluminum hydride in 25 ml of tetrahydrofuran. After 5 hours under reflux, a second 0.36 g portion of hydride is added and refluxing is then continued overnight. The reaction medium is then cooled and hydrolyzed with 0.55 ml of water, then with 0.45 ml of 20% strength sodium hydroxide and thereafter with 2 ml of water. The aluminum salts are then filtered off and rinsed with tetrahydrofuran and the filtrate obtained is then evaporated to dryness. The dry residue is taken up with 1N hydrochloric acid and ethyl ether. The precipitate obtained is filtered off, dried adn then recrystallized in methanol.

Yield: 34%.

Melting point: >260° C. (sublimation).

The NMR spectrum of the hydrochloride is shown in Table I.

EXAMPLE 35 dl-7-[N-(2,2,2-Trifluoroethyl)amino]-2,3,5,6,7,8-hexahydronaphtho[2,3-b]furan hydrochloride

STAGE A dl-7-(Trifluoroacetylamino)-2,3,5,6,7,8-hexahydronaphtho[2,3-b]furan

A mixture containing 5 g of the compound of Example 2, 3.35 ml of triethylamine and 4 ml of ethyl trifluoroacetate in 7 ml of methanol is stirred for 4 hours at room temperature. The mixture is then evaporated to dryness and the dry residue obtained is recrystallized in isopropyl ether.

Yield: 50%.

Melting point: 131° C.

NMR spectrum (CDCl$_3$): 1.5 to 2.3 ppm,m,2H; 2.3 to 3.5 ppm,m,6H; 3.8 to 4.5 ppm,m,1H; 4.5 ppm,t,2H; 5.4 to 7.0 ppm,m,1H; 6.5 ppm,s,1H; 6.95 ppm,s,1H.

STAGE B

This compound is prepared from a compound obtained in the preceding stage and according to the process described in Example 34, Stage B. The reaction time with lithium aluminum hydride is approximately 2 hours 30 minutes.

Yield: 26%.

Melting point: >260° C.

The NMR spectrum of the compound is shown in Table I.

EXAMPLE 36 dl-7-[N-n-Propyl-N-(2-thienylethyl)amino]-2,3,5,6,7,8-hexahydronaphtho[2,3-b]furan hydrochloride

STAGE A dl-7-[N-n-Propyl-N-(2-thienylacetyl)amino]-2,3,5,6,7,8-hexahydronaphtho[2,3-b]furan A solution of (2-thienyl)acetyl chloride in 15 ml of benzene is added dropwise to a solution of 13 g of the compound of Example 34 in 160 ml of benzene and 10.2 g of triethylamine. After being stirred at room temperature for 3 hours, the mixture is diluted with water, extracted with anhydrous sodium acetate and then evaporated under vacuum. After passage through a silica column using a mixture of methylene chloride and ethyl acetate (95:5) as eluant, 4 g of oil are obtained.

Yield: 22%.

NMR spectrum (CDCl$_3$): 0.95 ppm,t,3H; 1.3 to 2.2 ppm,m, 4H; 2.7 to 3.5 ppm,m,9H; 4.0 ppm,s,2H; 4.60 ppm,t,2H; 6.55 ppm,s,1H; 7.0 ppm,m,3H; 7.2 to 7.4 ppm,m,1H.

STAGE B

The expected hydrochloride is obtained from the compound obtained in Stage A described above and using the process described in Example 34, Stage B.

Yield: 50%.

The NMR spectrum of this compound is shown in Table I.

EXAMPLE 37 dl-7-(2-Oxo-1-pyrrolidinyl)-2,3,5,6,7,8-hexahydronaphtho-[2,3-b]furan

STAGE A 7-(4-Chlorobutyramido)-2,3,5,6,7,8-hexahydronaphtho[2,3-b]furan 4.2 g of 4-chlorobutyryl chloride are added at room temperature to a mixture of 5 g of the compound of Example 2 and 4.2 g of triethylamine in 60 ml of benzene. After 1 hour at room temperature, the medium is diluted with water and filtered and the aqueous phase is extracted with benzene. The filtrate and the precipitate are combined and the benzene is evaporated off under vacuum. The dry residue is solidified in ether.

Yield: 60%.

Melting point: 135° C.

NMR spectrum (CDCl$_3$): 0.95 ppm,t,3H; 1.3 to 2.2 ppm,m, 4H; 2.7 to 3.5 ppm,m,9H; 4.00 ppm,s,2H; 4.60 ppm,t,2H; 6.55 ppm,s,1H; 7.0 ppm,m,3H; 7.2 to 7.4 ppm,m,1H.

STAGE B

A mixture of 3.3 g of the compound described above is brought to reflux for 6 hours with 0.32 g of sodium hydride at a concentration of 50% in tetrahydrofuran. After being cooled, the mixture is diluted with water and extracted with ethyl ether and the extract washed with 1N hydrochloric acid and then with water to neutrality. The organic phase is evaporated to dryness and the residue washed with cyclohexane and then recrystallized in methyl ethyl ketone.

Yield: 35%.

Melting point: 131°-133° C.

The spectrum of this compound is shown in Table I.

EXAMPLE 38 d-7-(N-Methylamino)-2,3,5,6,7,8-hexahydronaphtho[2,3-b]furan hydrochloride

STAGE A

7-(N-Methylamino)-2,3,5,6,7,8-hexahydronaphtho[2,3-b]furan dibenzoyltartrate

This salt was obtained by reacting the compound of Example 9 with a half-equimolar quantity of l-dibenzoyltartaric acid. After a recrystallization from ethanol and a recrystallization from methanol followed by 3 recrystallizations in a mixture of methanol and water (1:1), the salt is obtained optically pure.

Melting point: 210°–215° C.

STAGE B

The dibenzoyltartrate obtained in the preceding stage is suspended in ethyl ether and alkalinized with sodium hydroxide. The organic phase is separated, dried over anhydrous sodium sulfate and evaporated. The oil obtained is taken up in acetonitrile and a stoichiometric quantity of ethereal hydrogen chloride is then added to obtain the hydrochloride.

Melting point: 257°–260° C.

Rotatory power of a 0.25% strength solution in DMSO:

| $\lambda$ nm | $[\alpha]_D^{23°\ C.}$ |
| --- | --- |
| 589 | +84.6 |
| 578 | +89.0 |
| 546 | +102.0 |
| 436 | +187.0 |
| 365 | +339.0 |

EXAMPLE 39 l-7-(N-Methylamino)-2,3,5,6,7,8-hexahydronaphtho[2,3-b]furan hydrochloride

This hydrochloride was obtained according to the process described above, but using d-dibenzoyltartaric acid.

Melting point: 258°–260° C.

Rotatory power of a 0.25% strength solution in DMSO:

| $\lambda$ nm | $[\alpha]_D^{23°\ C.}$ |
| --- | --- |
| 589 | −89.2 |
| 578 | −92.4 |
| 546 | −106.8 |
| 436 | −194.0 |
| 365 | −351.4 |

EXAMPLE 40 d-7-(N,N-Dimethylamino)-2,3,5,6,7,8-hexahydronaphtho-[2,3-b]furan hydrochloride

STAGE A d-7-(N,N-Dimethylamino)-2,3,5,6,7,8-hexahydronaphtho-[2,3-b]furan tartrate

This salt was obtained by reacting the compound of Example 6 with an equimolar quantity of l-tartaric acid. After 7 recrystallizations in water, the salt is obtained optically pure.

Melting point: 95°–100° C.

Rotatory power of a 0.25% strength solution in DMSO:

| $\lambda$ nm | $[\alpha]_D^{23°\ C.}$ |
| --- | --- |
| 589 | +52.1 |
| 578 | +54.6 |
| 546 | +62.0 |
| 436 | +110.0 |
| 365 | +193.1 |

STAGE B

The tartrate obtained in the preceding stage is dissolved in ethyl acetate and then alkalinized with sodium hydroxide. The organic phase is separated, dried over anhydrous sodium sulfate and evaporated. The oil obtained is taken up in ethanol and a stoichiometric quantity of ethereal hydrogen chloride is then added to obtain optically pure d-7-(N,N-dimethylamino)-2,3,5,6,7,8-hexahydronaphtho[2,3-b]furan hydrochloride.

Melting point: 226°–228° C.

Rotatory power of a 0.25% strength solutioin in DMSO:

| $\lambda$ nm | $[\alpha]_D^{23°\ C.}$ |
| --- | --- |
| 589 | +90.5 |
| 578 | +94.9 |
| 546 | +109.1 |
| 436 | +200.8 |
| 365 | +365.6 |

EXAMPLE 41 l-7-(N,N-Dimethylamino)-2,3,5,6,7,8-hexahydronaphtho-[2,3-b]furan hydrochloride This hydrochloride was obtained according to the process described in Example 40, but using d-tartaric acid in Stage A.

Melting point: 226°–228° C.

Rotatory power of a 0.25% strength solution in DMSO:

| $\lambda$ nm | $[\alpha]_D^{23°\ C.}$ |
| --- | --- |
| 589 | −91.1 |
| 578 | −95.9 |
| 546 | −110.4 |
| 436 | −201.9 |
| 365 | −367.1 |

TABLE I

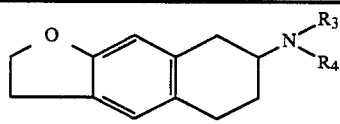

| EX. | R3 | R4 | NMR (solvent) |
|---|---|---|---|
| 2 | H | H | (CDCl$_3$+DMSO—d$_6$) 1.7–3.7 ppm,m,9H; 4.6 ppm,t,2H; 6.5 ppm,m,1H; 7 ppm,m,1H; 8.65 ppm,3H, exchangeable |
| 5 | —CH$_2$CH$_2$CH$_3$ | —CH$_2$CH$_2$CH$_3$ | (CDCl$_3$) 0.8 ppm,t,6H; 1.6 ppm,m,6H; 2 ppm,m,1H;2.3 to 2.8 ppm,m,8H; 3.1 ppm,t,2H; 4 a 5 ppm,t,2H; 6.5 ppm, s,1H; 6.8 ppm,s,1H |
| 6 | —CH$_3$ | —CH$_3$ | (CDCl$_3$) 1.2 to 2.5 ppm, m,2H; 2.3 ppm,s,6H; 2.5 to 3.2 ppm, m,5H; 3.1 ppm,t,2H; 4.5 ppm, t,2H; 6.5 ppm,s,1H; 6.9 ppm,s,1H |
| 7 | H | —CH$_2$—C$_6$H$_5$ | (CDCl$_3$). 1.6 ppm, 1H, exchangeable; 1.3 to 2.3 ppm,m,2H; 2.5 to 3.2 ppm,m,1H; 3.1 ppm,t,2H; 3.9 ppm,s,2H; 4.5 ppm,t,2H; 6.6 ppm,s,1H; 7.0 ppm,s,1H; 7.4 ppm,s,5H |
| 8 | —CH$_3$ | —CH$_2$—C$_6$H$_5$ | (CDCl$_3$) 1.2 to 2.3 ppm,m,2H; 2.3 ppm,m,3H; 2.5 to 3.1 ppm, m,5H; 3.1 ppm,t,2H; 3.7 ppm,s,2H; 4.5 ppm,t,2H; 6.6 ppm,s,1H 7.0 ppm,s,1H; 7.4 ppm,m,5H |
| 9 | —CH$_3$ | H | (CDCl$_3$+DMSO—d$_6$) 1.9 to 2.5 ppm,m,2H; 2.5 to 3.9 ppm,m,10H; 4.5 ppm, t,2H; 6.5 ppm,s,1H; 7.0 ppm,s,1H; 9.7 ppm,2H, exchangeable |
| 10 | —CH$_3$ | —CH$_2$—C$_6$H$_{11}$ | (CDCl$_3$) 1 to 2.5 ppm,m,13H; 2.7 a 3.8 ppm,m,12H; 4.5 ppm, t,2H; 6.5 ppm,s,1H;6.9 ppm,s,1H |
| 11 | —H | —CH$_2$—(CH$_2$)$_5$—COO—C$_2$H$_5$ | (CDCl$_3$) 1.2 ppm,t,3H; 1.2 to 2.6 ppm,m,12H; 2.6 to 3.6 ppm,m,9H; 4.2 ppm,q,2H; 4.5 ppm,t,2H; 6.5 ppm,s,1H; 7.0 ppm,s,1H; 9.8 ppm,2H, exchangeable |
| 12 | —H | —CH$_2$—(CH$_2$)$_5$—COOH | (DMSO—d$_6$) 1 to 2.1 ppm,m,10H; 2 to 2.5 ppm,m,2H; 2.5 to 3.8 ppm,m,11H (exchangeable 2H); 4.5 ppm,t,2H; 6.6 ppm,s,1H; 7 ppm,s,1H; 9 to 10.5 ppm,m,1H, exchangeable |
| 13 | —H | —CH$_2$CH$_2$OC$_2$H$_5$ | (CDCl$_3$) 1.2 ppm,t,3H; 1.7 ppm,1H, exchangeable, 1.4 to 2.5 ppm,m,2H; 2.6 a 3.4 ppm,t+m,2+7H; 3.3 to 3.8 ppm, q+t,4H; 4.55 ppm,t,2H; 6.55 ppm,s,1H; 6.95 ppm,s,1H |
| 14 | —H | —CH$_2$CH$_2$OH | (CDCl$_3$) 1.75 ppm 2H, exchangeable; 1.4 to 2.5 ppm,m,2H; 2.5 to 3.8 ppm,t,2H,m,6H,m,2H,m,1H; 4.5 ppm,t,2H;6.6 ppm,s,1H; 7 ppm,s,1H |
| 24 | —H | —CH$_2$—(CH$_2$)$_4$COOC$_2$H$_5$ | (DMSO—d$_6$) 1.21 ppm,t,3H; 1.4 to 2.0 ppm,m,8H; 2.0 to 2.5 ppm, m,5H; 2.5 to 3.4 ppm,m,6H; 4.0 ppm,q,2H; 4.4 ppm, t,6.45 ppm,s,1H; 6.90 ppm,s,1H; 9.25 ppm 2H exchangeable |
| 25 | —H | —CH$_2$—(CH$_2$)$_4$COOH | (DMSO—d$_6$) 1.2 to 4 ppm,m,+t,+m,+t,+m,8+2+6+2+1H; 4.5 ppm,t,2H; 6.6 ppm,s,1H; 7 ppm,s,H; 8 to 11.5 ppm,3H, exchangeable |
| 26 | —H | —CH(CH$_3$)—(CH$_2$)$_3$COOC$_2$H$_5$ | (CDCl$_3$) 1 to 1.3 ppm,t,+d,3+3H; 1.4 ppm, 1H, exchangeable; 1.2 to 3 ppm,m,+m,+m,4+2+6H; 3.1 ppm,t,2H; 3 to 4 ppm, m,+t,2+2H; 4 to 4.4 ppm,q,2H; 4.5 ppm,t,2H; 6.6 ppm,s,1H; 7 ppm,s,1H |
| 27 | —H | —CH(CH$_3$)—(CH$_2$)$_3$COOH | (D$_2$O+DCl) 1.4 ppm,d,3H; 1.5 to 4 ppm,t,+m,2+2H; 4.6 ppm,t,2H; 6.6 ppm,t,+s,2+1H; 7 ppm,s,1H |

TABLE I-continued

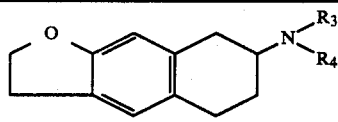

| EX. | R₃ | R₄ | NMR (solvent) |
|---|---|---|---|
| 28 | —H | —CH(CH₃)—(CH₂)₄COOC₂H₅ | (CDCl₃) 1 to 2 ppm,t,+d,+t,3+3+8H; 2 to 3.7 ppm,t,+m,+t,+m,2+4+ 2+2H; 4.1 ppm,q,2H; 4.5 ppm,t,2H; 6.6 ppm,s,1H; 7 ppm,s,1H; 9.3 ppm,2H, exchangeable |
| 29 | —H | —CH(CH₃)—(CH₂)₄COOH | (DMSO—d₆) 1 to 2 ppm,d,+m,3+8H; 2 to 2.5 ppm,m,2H; 2.5 to 3.8 ppm,m,2H; 4.5 ppm,t,2H; 6.6 ppm,s,1H; 7.05 ppm,s, 1H; 8 to 11 ppm,3H, exchangeable |
| 30 | —H | —CH(CH₃)—(CH₂)₅COOC₂H₅ | (DMSO—d₆) 1 to 2 ppm,t,+d,+m,3+3+10H; 2 to 3.7 ppm,t,+m,+t,+m, 2+4+2+2H; 4.08 ppm,q,2H; 4.5 ppm,t,2H; 6.5 ppm,s,1H; 7 ppm,s,1H; 9.1 ppm,2H, exchangeable |
| 31 | —H | —CH(CH₃)—(CH₂)₅COOH | (DMSO—d₆) 1 to 2 ppm,t,+d,+m,2+3+10H; 2 to 2.5 ppm,m,2H; 2.5 to 3.8 ppm,m,+t,+m,4+2+2H; 4.5 ppm,t,2H; 6.6 ppm,s,1H; 7.05 ppm,s,1H; 8 to 11 ppm, 3H, ex changeable |
| 32 | —H | —CH₂—(CH₂)₅OH | (DMSO—d₆) 1 to 2.3 ppm,m,10H; 2.3 to 3.8 ppm, 1H, exchangeable+ m,+m,+t,+t,+m,2+4+2+2+1H; 4.5 ppm,t,2H; 6.6 ppm,s,1H; 7 ppm,s, 1H; 9 to 9.6 ppm, 2H, exchangeable |
| 33 | —H | —CH₂—CH=CH₂ | (D₂O+DCl) 1.4 to 2.5 ppm,m,2H; 2.5 to 3.9 ppm,m,+t,+m,+d, 4+2+1+2H; 4.5 ppm,t,2H; 5 to 6.5 ppm,t,+m,2+2H; 6.6 ppm,s,1H; 7.1 ppm,s,1H |
| 34 | —H | —CH₂CH₂CH₃ | (CD₃OD) 1.05 ppm,t,3H; 1.4 to 2.6 ppm,m,4H; 2.6 a 3.9 ppm, m,+t,+m,+m,4H+2H+2H+1H; 4.5 ppm,t,2H; 6.55 ppm,s,1H; 7 ppm,s,1H |
| 35 | —H | —CH₂CF₃ | (DMSO) 1.5 to 3.7 ppm,m,+m,+t,2+4+2H; 4.1 ppm,q,2H; 4.5 ppm,t,2H; 6.5 ppm,s,1H; 7 ppm,s,1H; 7 to 12 ppm,2H, exchangeable |
| 36 | —CH₂CH₂CH₃ | —CH₂CH₂—(2-thienyl) | (CDCl₃) 0.7 to 2.2 ppm,t,+m,3+4H; 2.3 to 3.6 ppm,m,+m,+m,+t, 4+6+1+2H; 4.5 ppm,t,2H; 6.55 ppm,s,1H; 6.7 to 7.4 ppm,s,+m,1+3H |
| 37 | | (2-oxocyclopentyl) | (CDCl₃) 1.5 to 2.7 ppm,m,+m,4+2H; 2.5 to 3 ppm,m,4H; 3.2 ppm,t,2H; 3.3 ppm,t,2H; 4 to 4.6 ppm,m,1H; 4.5 ppm,t,2H; 6.5 ppm,s,1H; 6.9 ppm,s,1H |

PHARMACOLOGICAL STUDY

Example 42

Antagonism of apomorphine-induced rearing-up behavior

Studied in the test of antagonism of apomorphine-induced rearing-up following the subcutaneous administraton of a dose of 0.75 mg.kg⁻¹ of this substance in mice, the compounds of general formula I act in a clear-cut manner at doses greater than or equal to 2.5 mg.kg⁻¹ (i.p.). The same results are observed when the compounds of general formula I are administered orally at a dose of 20 mg.kg⁻¹. The activity of the compounds was assessed according to the method described by Protais P, Costentin J and Schwartz J. C. in Psychopharmacology (1976), 50, p. 1–6. The results of this trial are reported in Tables II and III.

(s=significant difference, p <0.05).

TABLE II

| | % INHIBITION OF REARING-UP FOR AN i.p. DOSE (mg.kg⁻¹) | | | | |
|---|---|---|---|---|---|
| COMPOUND | 2.5 | 5 | 10 | 20 | 40 |
| Example 2 | | −56[s] | −58[s] | −91[s] | −100[s] |
| Example 3 | | | −72[s] | −79[s] | |
| Example 4 | | | −24 | −86[s] | |
| Example 5 | | | | +27 | −54[s] |
| Example 6 | −17 | −54[s] | −94[s] | −100[s] | |
| Example 9 | −46[s] | −65[s] | −100[s] | −100[s] | |
| Example 10 | | | +11 | +11 | −96[s] |
| Example 12 | | | −17 | −20 | |
| Example 15 | | | | −9 | 0 |
| Example 18 | | | | −12 | +6 |
| Example 19 | | | | −57 | −90[s] |

TABLE II-continued

| COMPOUND | % INHIBITION OF REARING-UP FOR AN i.p. DOSE (mg.kg$^{-1}$) | | | | |
|---|---|---|---|---|---|
| | 2.5 | 5 | 10 | 20 | 40 |
| Example 21 | | | −56$^s$ | −84$^s$ | |
| Example 27 | | | −46$^s$ | −63$^s$ | |
| Example 31 | | | | +5 | +22$^s$ |
| Example 32 | | | | −32 | −40$^s$ |
| Example 34 | | | −23 | −32 | −100$^s$ |
| Example 35 | | | −30 | −38 | |
| Example 38 | −76$^s$ | −100$^s$ | | | |
| Example 40 | −75$^s$ | −100$^s$ | | | |

TABLE II

| COMPOUND | % INHIBITION OF REARING-UP FOR A p.o. DOSE (mg.kg$^{-1}$) | |
|---|---|---|
| | 10 | 20 |
| 2 | −77$^s$ | −100$^s$ |

EXAMPLE 43

Antagonism of apomorphine- or amphetamine-induced stereotypy

The inhibitary activity of the compounds of the invention with respect to apomorphine- or amphetamine-induced stereotypy in rats was assessed using the scale of scoring of stereotyped movements described by Quinton R. M. and Halliwell G. in Nature (1963), 200, p. 178–179.

Apomorphine or amphetamine was administered to the animals intraperitoneally at a dose of 1.5 mg.kg$^{-1}$. The percentage inhibition (−) or potentiation (+) of the stereotypy score (% ISS) shown in Tables IV and V for apomorphine corresponds to a measurement time of 30 minutes. In contrast, the percentage inhibition of the stereotypy score shown in Table VI for amphetamine corresponds to a measurement time of 3 hours.

(s=signifcant difference, p<0.05).

TABLE IV

| COMPOUND | % ISS FOR AN i.p. DOSE mg.kg$^{-1}$ | | |
|---|---|---|---|
| | 5 | 10 | 20 |
| Example 2 | −16 | −62$^s$ | −48$^s$ |
| Example 5 | −3 | 0 | |
| Example 6 | | −48$^s$ | −58$^s$ |
| Example 12 | | +19 | −3 |
| Example 25 | | +9 | |
| Example 27 | | −5 | −8 |
| Example 29 | | +11 | |
| Example 31 | | +5 | −3 |
| Example 32 | | −3 | −5 |
| Example 34 | | −68$^s$ | −70$^s$ |
| Example 37 | | −6 | −14 |
| Example 38 | −60$^s$ | −54$^s$ | |
| Example 40 | | −61$^s$ | −67$^s$ |
| Example 41 | | +11 | +3 |

TABLE V

| COMPOUND | % ISS FOR A p.o. DOSE mg.kg$^{-1}$ | |
|---|---|---|
| | 10 | 20 |
| Example 2 | −55$^s$ | −55$^s$ |

TABLE VI

| COMPOUND | % ISS FOR AN i.p. DOSE mg.kg$^{-1}$ | |
|---|---|---|
| | 5 | 10 |
| Example 2 | +32$^s$ | +39$^s$ |

TABLE VI-continued

| COMPOUND | % ISS FOR AN i.p. DOSE mg.kg$^{-1}$ | |
|---|---|---|
| | 5 | 10 |
| Example 12 | +11 | +14$^s$ |

EXAMPLE 44

Antagonism with respect to apomorphine-induced hypothermia

Testing for an antagonism with respect to apomorphine-induced hypothermia in mice was performed according to the method described by CHERMAT R. and PONCELET M. in J. Pharmac. (1983), 14, No. 1, p. 93–97. The dose of apomorphine administered subcutaneously was 1 mg.kg$^{-1}$. Tables VII and VIII show the percentage antagonism of the hypothermia observed after 2 hours.

(s=significant, p<0.05).

TABLE VII

| COMPOUND | % ANTAGONISM OF HYPOTHERMIA FOR AN i.p. DOSE | | | | |
|---|---|---|---|---|---|
| | 1 | 2.5 | 5 | 10 | 20 |
| Example 2 | −11 | | −57$^s$ | −54$^s$ | −80$^s$ |
| Example 3 | | −72$^s$ | −79$^s$ | −91$^s$ | −86$^s$ |
| Example 4 | | −8 | −3 | −11 | −19 |
| Example 5 | | | −20 | −47$^s$ | −68$^s$ |
| Example 6 | | +6 | −6 | −25$^s$ | −48$^s$ |
| Example 9 | | −39$^s$ | −67$^s$ | −86$^s$ | −84$^s$ |
| Example 12 | | | | −4 | −2 |
| Example 27 | | | | −5 | −32$^s$ |
| Example 32 | | | | −10 | −13 |
| Example 34 | | | | −7 | −16 |
| Example 35 | | | | −16 | −31$^s$ |
| Example 38 | | −48$^{s/}$ −91$^s$ | −112$^s$ | −119$^s$ | |
| Example 40 | | | | −44$^s$ | −73$^s$ |

TABLE VIII

| COMPOUND | % ANTAGONISM OF HYPOTHERMIA FOR A p.o. DOSE | | | |
|---|---|---|---|---|
| | 2.5 | 5 | 10 | 20 |
| Example 2 | −35$^s$ | −59$^s$ | −70$^s$ | −86$^s$ |

EXAMPLE 45

Assessment of the antiaggressive effects

The antiaggressive effects of the compounds of the invention were investigated by two methods, one of them testing for an inhibition of aggressive behavior in previously isolated mice (Yen C. Y., Stanger A. L., and Millman N, Arch. Int. Pharmacodyn. Therap. (1959), 123, p. 179–185), and the other in isolated and bulbectomized rats (Garattini S. and Sigg E. B. "Aggressive Behaviour" p. 47–55 Ed. Excerpta Medica Found., Amsterdam, 1969). The compounds of the invention, administered intraperitoneally, significantly inhibit isolation-induced aggression in mice and the aggression of isolated, bulbectomized rats.

(Tables IX and X, s=significant, p<0.05).

TABLE IX

| COMPOUND | % OF PAIRS OF MICE SHOWING NO SIGN OF FIGHTING DOSE mg.kg$^{-1}$ | | | | |
|---|---|---|---|---|---|
| | 2.5 | 5 | 10 | 20 | 40 |
| Example 2 | 40$^s$ | 70$^s$ | 100$^s$ | 100$^s$ | |
| Example 3 | 56$^s$ | 78$^s$ | | | |

TABLE IX-continued

% OF PAIRS OF MICE SHOWING NO SIGN OF FIGHTING DOSE mg.kg$^{-1}$

| COMPOUND | 2.5 | 5 | 10 | 20 | 40 |
|---|---|---|---|---|---|
| Example 4 | 22 | 44 | | | |
| Example 5 | | | | 50$^s$ | 89$^s$ |
| Example 6 | 40$^s$ | 44 | 78$^s$ | | |
| Example 9 | 67$^s$ | 56$^s$ | 89$^s$ | | |
| Example 10 | | 0 | 11 | 60$^s$ | |
| Example 25 | | | 20 | | |
| Example 32 | | 10 | | 30 | |
| Example 38 | | 70$^s$ | | | |
| Example 39 | 70$^s$ | 90$^s$ | | | |
| Example 40 | | 22 | 50$^s$ | | |
| Example 41 | | 66$^s$ | 90$^s$ | | |

TABLE X

% OF RATS RENDERED NON-AGGRESSIVE DOSE mg.kg$^{-1}$

| COMPOUND | 1.25 | 2.5 | 5 | 10 |
|---|---|---|---|---|
| Example 2 | 17 | 50 | 73$^s$ | 17 |
| Example 3 | | 64$^s$ | | |
| Example 4 | | 12 | | |
| Example 6 | | 30 | | |
| Example 9 | | 27 | 58$^s$ | |
| Example 38 | | 37 | 75$^s$ | |
| Example 39 | | | 58$^s$ | |
| Example 40 | | | | 42$^s$ |
| Example 41 | | | | 50$^s$ |

EXAMPLE 46

Assessment of the antidepressant effects

The antidepressant effects of the compounds of the invention were investigated by assessing the antagonism of reserpine-induced hypothermia and the antagonism of the ponto-geniculo-occipital waves induced by the compound Ro4-1284 in cats.

1. Antagonism of reserpine-induced hypothermia

The study is carried out on Swiss CD male mice (27-28 g). After distribution into groups of 10 animals each, reserpine is injected intraperitoneally at a dose of 2.5 mg.kg$^{-1}$. Three hours later, the compounds undergoing trial are administered intraperitoneally. The rectal temperature of the animals is measured one hour and two hours after the second treatment, and compared with the initial termperature To of these same animals, measured immediately before the administration of the compounds undergoing trial.

2. Antagonism of the ponto-geniculo-occipital (P.G.O.) waves induced by Ro4-1284

This study was performed according to the method of Ruch-Monachon M. A., Jalfre M. and Haefely W. described in Arch. Int. Pharm. Therap., (1976), 219, No. 2, p. 251-346, and it enabled the effective dose (i.v.) inhibiting by 50% (ED$_{50}$) the number of P.G.O. waves to be assessed.

The results of these studies are shown in Tables XI and XII (s=p<0.05).

TABLE XI

% INHIBITION OF HYPOTHERMIA DOSE mg.kg$^{-1}$ i.p.

| COMPOUND | 2.5 | 5 | 10 | 20 |
|---|---|---|---|---|
| Example 2 | −62$^s$ | −27 | −32$^s$ | −47$^s$ |
| Example 6 | −1 | +1 | −24 | −20 |
| Example 9 | −8 | +37 | +16 | +11 |
| Example 12 | | −23 | −45$^s$ | −18 |
| Example 27 | | | −13 | −21 |
| Example 32 | | | −1 | −29$^s$ |
| Example 35 | | | −20 | −4 |
| Example 38 | −28 | −35 | −21 | |
| Example 39 | +37 | +14 | +6 | +15 |
| Example 40 | | | +14 | +14 |
| Example 41 | | | +13 | +29$^s$ |

TABLE XII

| COMPOUND | ED$_{50}$ (mg.kg$^{-1}$ i.v.) |
|---|---|
| Example 2 | 0.146 |
| Example 3 | 0.130 |
| Example 6 | 0.498 |
| Example 9 | 0.173 |
| Example 12 | > 2.52 |

EXAMPLE 47

Drug discrimination in rats

The dopamine-stimulating property of the compounds of the invention was demonstrated by drug discrimination experiments in rats. Rats were trained to discriminate between the effects of the interoceptive stimulus of apomorphine (0.2 mg.kg$^{-1}$ i.p.) and that of physiological saline, according to a principle described by Colpaert F. in "Drug discrimination application in C.N.S. Pharmacology" Ed. Elsevier Biomedical 1982, Amsterdam. After the training period, the compounds of the invention were administered to the animals intraperitoneally at a dose of 2.5 mg.kg$^{-1}$, in place of apomorphine, 30 minutes before the actual test.

Under the experimental conditions employed, the behavior shown by the animals coincides with that noted in the case of administration of apomorphine. The test compounds hence exert a generalization phenomenon in rats, which enables the conclusion to be drawn that they possess dopaminergic activity of an agonistic nature. The results of this study are shown in Table XIII.

TABLE XIII

| COMPOUND | DOSE mg. kg$^{-1}$ i.p. | NUMBER OF ANIMALS SHOWING THE EFFECT OF GENERALIZATION WITH APOMORPHINE | % OF ANIMALS WHICH GENERALIZE |
|---|---|---|---|
| Example 2 | 1.0 | 2/10 | 20 |
| Example 2 | 2.5 | 7/9 | 77 |
| Example 2 | 5.0 | 2/4 | 50 |
| Example 3 | 2.5 | 8/9 | 88 |
| Example 4 | 2.5 | 7/10 | 70 |

EXAMPLE 48
Gelatin capsules containing a 20-mg dose of dl-7-amino-2,3,5,6,7,8-hexahydronaphtho[2,3-b]furan hydrochloride
dl-7-Amino-2,3,5,6,7,8-hexahydronaphtho[2,3-b]furan
| hydrochloride | 20 mg |
|---|---|
| Cornstarch | 15 mg |
| Lactose | 25 mg |
| Talc | 5 mg |
For a No. 3 gelatin capsule.
Formula Chart No. 1
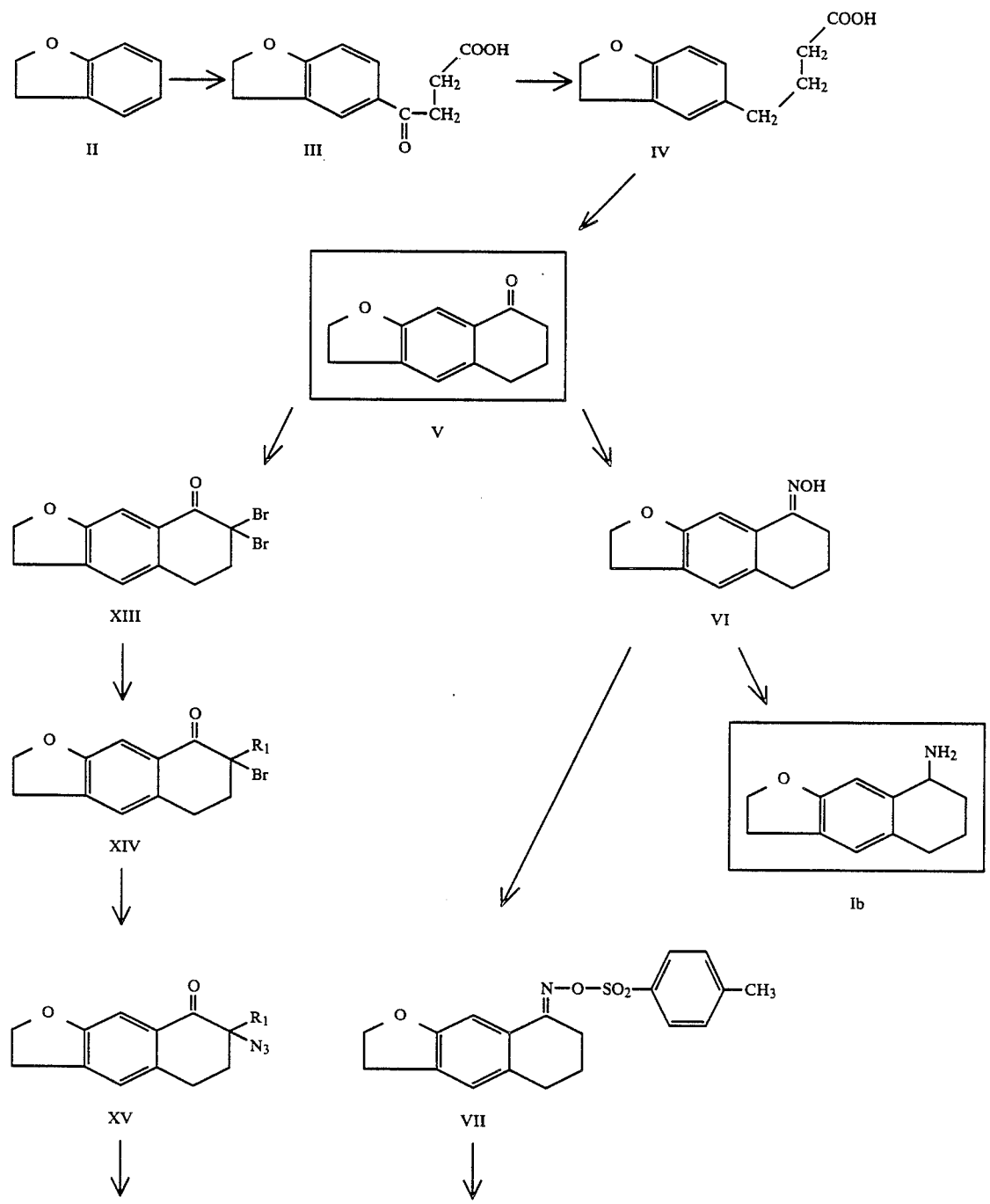

-continued
Formula Chart No. 1
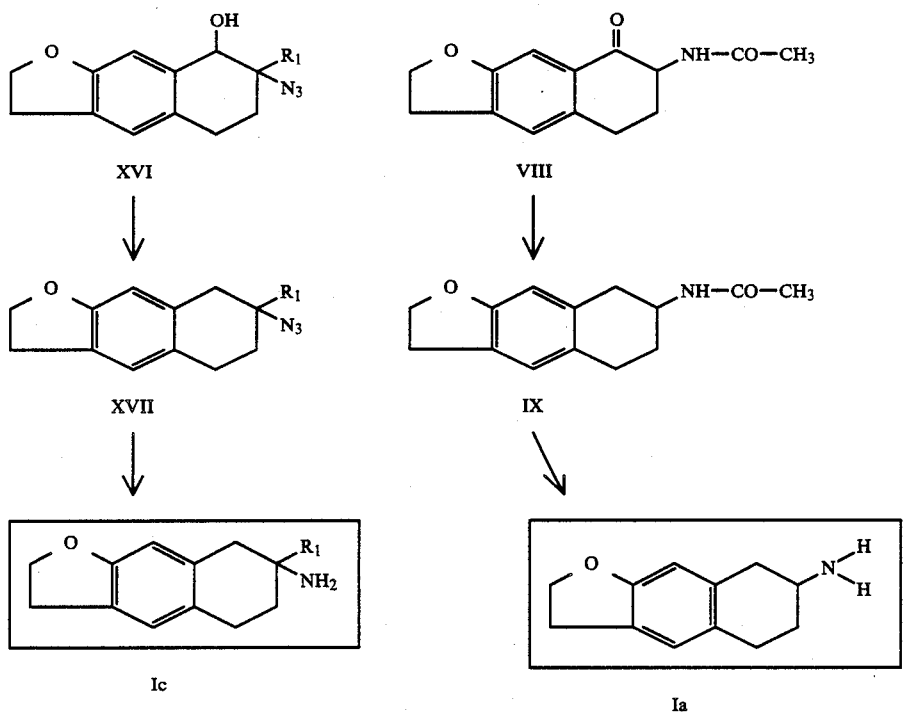
Formula Chart No. 2
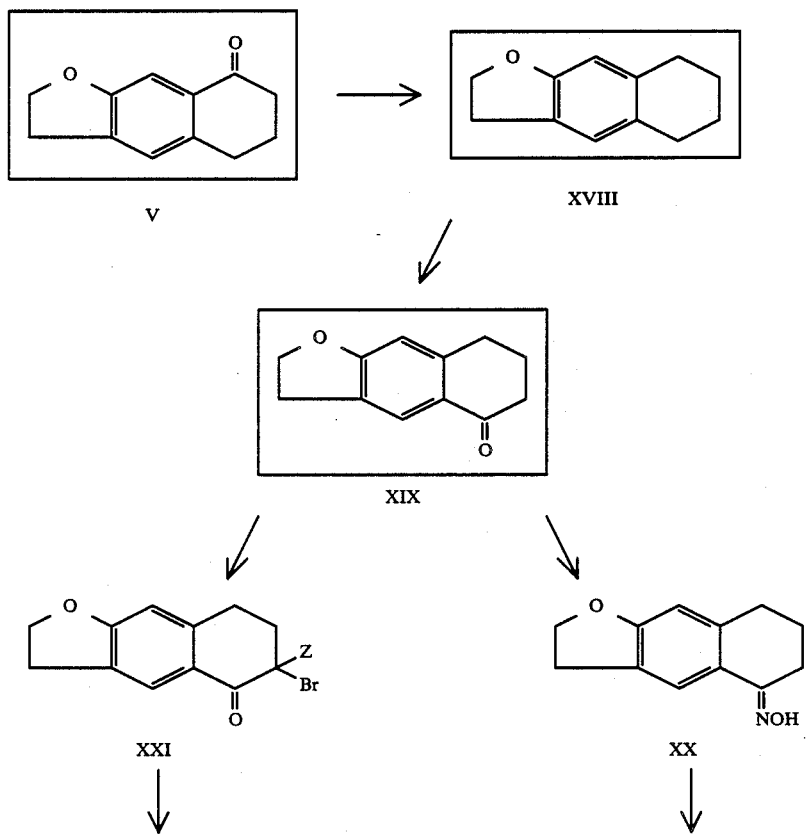

-continued
Formula Chart No. 2
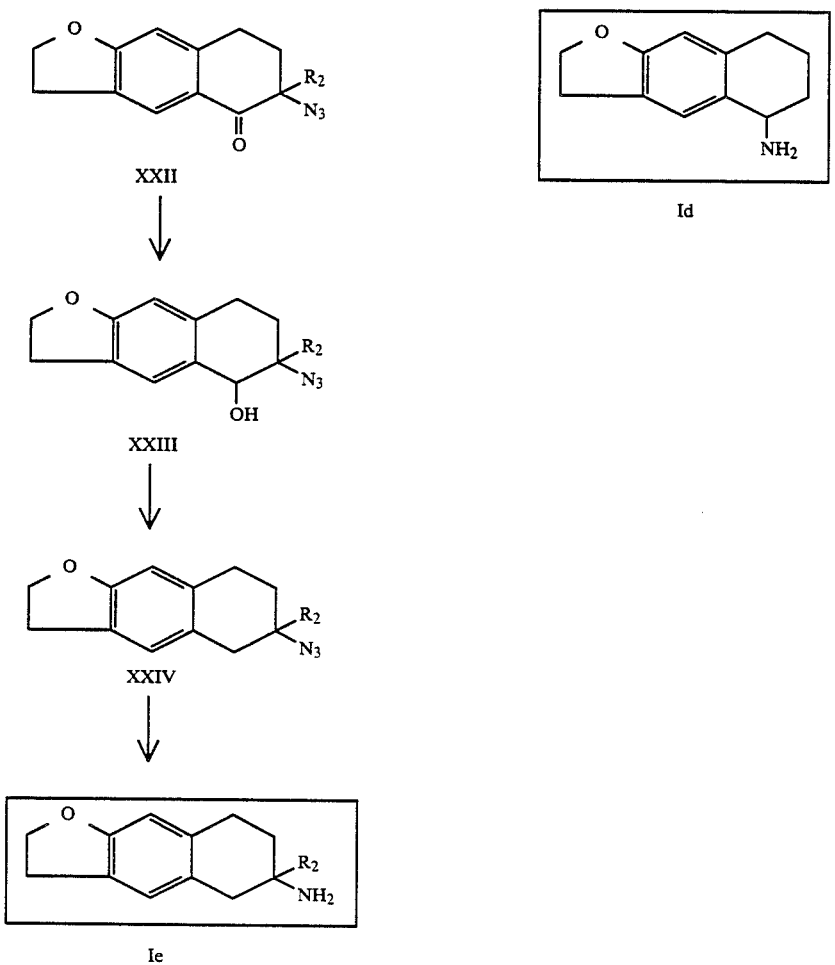
Formula Chart No. 3
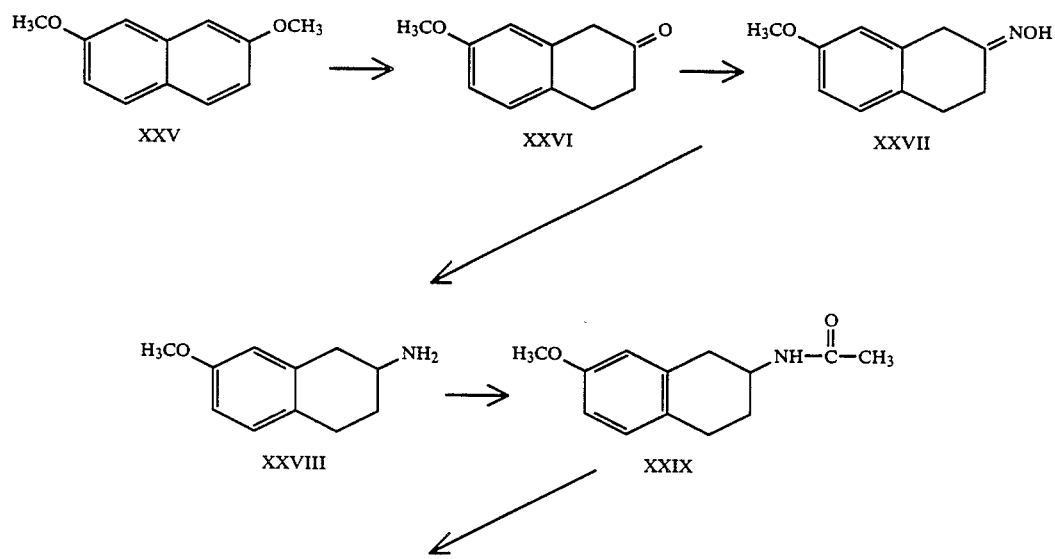

-continued
Formula Chart No. 3
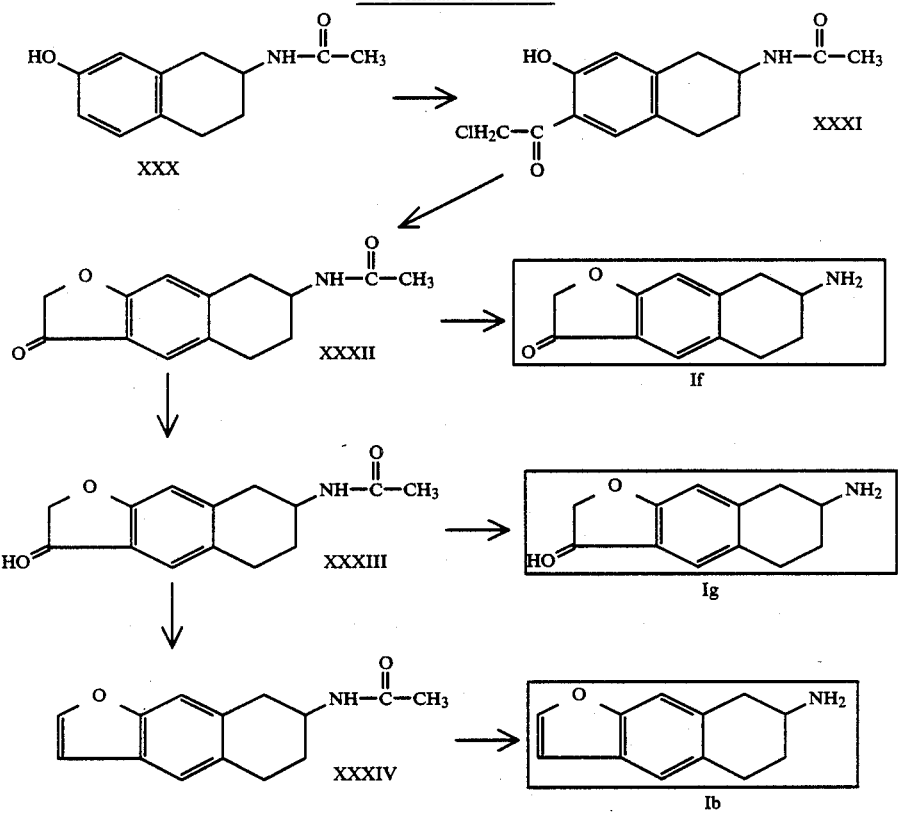
What is claimed is:
1. 2,3,5,6,7,8-Hexahydronaphtho[2,3-b]furan-5-one.
* * * * *

UNITED STATES PATENT AND TRADEMARK OFFICE
CERTIFICATE OF CORRECTION

PATENT NO. : 4,885,373

DATED : December 5, 1989

INVENTOR(S) : Jean L. Peglion, Jean C. Poignant, Joel Vian

It is certified that error appears in the above-identified patent and that said Letters Patent is hereby corrected as shown below:

Col. 1, line 26: "considerably" should read -- considerable --

Col. 2, line 22: delete "with"

Col. 4, line 42: "Xi" should read -- XI --

Col. 9, line 59: insert -- and -- after "$R_3$"

Col. 13, line 28: insert -- p. -- after "Ed.," and continue with "1374-1385" from line 29 (should be same paragraph)

Col. 13, line 40: "qual" should read -- gual --

Col. 13, line 57: insert -- b -- after "[2,3-"

Col. 15, line 55: insert -- ; 7.4 ppm, m, 1H. -- after "1H"

Col. 16, line 5: delete "L" after "($CDCL_3$):"

Col. 17, line 50: "20%" should read -- 10% --

Col. 22, line 42: insert -- 1 -- after "1.5"

Col. 23, line 49: delete "=" (both occurrences) and insert -- + -- (both occurrences)

Col. 24, line 44: insert -- b] -- after "2,3-"

Col. 26, line 54: "=" should read -- + --

Col. 27, line 46: "=" should read -- + --

Col. 27, line 68: "=" should read -- + --

Col. 29, line 45: "furan7-" should read -- furan-7- --

Col. 29, line 58: "amino}7-" should read -- amino}-7- --

Col. 30, line 16: "di" should read -- dl --

UNITED STATES PATENT AND TRADEMARK OFFICE
CERTIFICATE OF CORRECTION

PATENT NO. : 4,885,373

DATED : December 5, 1989

INVENTOR(S) : Jean L. Peglion, Jean C. Poignant, Joel Vian

It is certified that error appears in the above-identified patent and that said Letters Patent is hereby corrected as shown below:

Col. 30, line 50: "of" should read -- to --

Col. 31, line 16: delete "=" (all occurrences) and insert -- + -- (all occurrences)

Col. 31, line 32: "adn" should read -- and --

Col. 34, line 35: "solutioin" should read -- solution --

Col. 36, line 49 (approximately), Example 24, 4th column, 4th line: insert -- 2H; -- after "t,"

Col. 38, approximately line 17, Example 31, 4th column, 4th line: delete space between "ex" and "changeable"

Col. 40, approximately line 34, Example 38, Table VII, 3rd column: delete "/" after "s"

Col. 40, approximately line 34, Example 38, Table VII, 4th column: "$-112^s$" should read -- $-91^s$ --

Col. 40, approximately line 34, Example 38, Table VII, 5th column: "$-119^s$" should read -- $-112^s$ --

UNITED STATES PATENT AND TRADEMARK OFFICE
CERTIFICATE OF CORRECTION

PATENT NO. : 4,885,373

DATED : December 5, 1989           Page 3 of 3

INVENTOR(S) : Jean L. Peglion, Jean C. Poignant, Joel Vian

It is certified that error appears in the above-identified patent and that said Letters Patent is hereby corrected as shown below:

Col. 40, approximately line 34, Example 38, Table VII, 6th column: insert -- -119$^s$ --

Col. 40, approximately line 35, Table VII, 3rd column: delete "_91s"

Signed and Sealed this

Twentieth Day of November, 1990

*Attest:*

HARRY F. MANBECK, JR.

*Attesting Officer*         *Commissioner of Patents and Trademarks*